(12) United States Patent
Ye et al.

(10) Patent No.: US 8,053,095 B2
(45) Date of Patent: Nov. 8, 2011

(54) COMPOUND COMPRISING PHENYL PYRIDINE UNITS

(75) Inventors: Qing Ye, Los Gatos, CA (US); Jie Liu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/055,121

(22) PCT Filed: Jun. 5, 2009

(86) PCT No.: PCT/US2009/046372

§ 371 (c)(1),
(2), (4) Date: Jan. 20, 2011

(87) PCT Pub. No.: WO2010/011426

PCT Pub. Date: Jan. 28, 2010

(65) Prior Publication Data

US 2011/0121235 A1    May 26, 2011

(30) Foreign Application Priority Data

Jul. 24, 2008   (CN) .......................... 2008 1 0134449

(51) Int. Cl.
*H01L 51/54* (2006.01)
*C09K 11/06* (2006.01)
*C07F 5/02* (2006.01)

(52) U.S. Cl. ........ 428/690; 428/917; 313/504; 313/506; 546/13; 546/15; 546/256; 546/261; 546/255; 252/301.16

(58) Field of Classification Search .................. None
See application file for complete search history.

(56) References Cited

FOREIGN PATENT DOCUMENTS

| JP | 2004-014440 | * | 1/2004 |
| WO | 2005/062676 A | | 7/2005 |

OTHER PUBLICATIONS

Search Report and Written Opinion issued in connection with corresponding WO Patent Application No. PCT/US09/46372 filed on Jun. 5, 2009.

* cited by examiner

*Primary Examiner* — Dawn L Garrett
(74) *Attorney, Agent, or Firm* — GE Global Patent Operation; Peter T. DiMauro

(57) ABSTRACT

Compounds of formula I may be used in optoelectronic devices

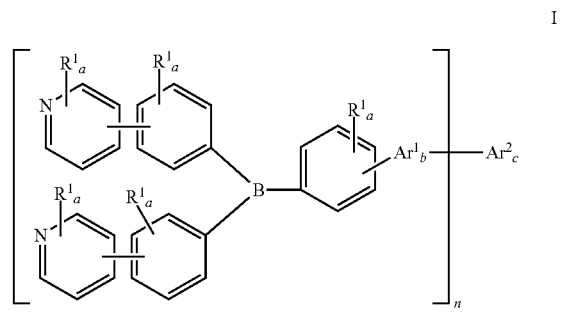

wherein
$R^1$ is, independently at each occurrence, a $C_1$-$C_{20}$ aliphatic radical, a $C_3$-$C_{20}$ aromatic radical, or a $C_3$-$C_{20}$ cycloaliphatic radical;
a is, independently at each occurrence, an integer ranging from 0-4;
b is 0, 1 or 2;
$Ar^1$ is a direct bond or heteroaryl, aryl, or alkyl or cycloalkyl;
$Ar^2$ is heteroaryl, aryl, or alkyl or cycloalkyl;
c is an integer ranging from 1-7; and
n is an integer ranging from 2-4.

23 Claims, No Drawings

COMPOUND COMPRISING PHENYL PYRIDINE UNITS

BACKGROUND

The invention relates generally to compounds, and particularly to compounds comprising phenyl pyridine units and optoelectronic devices using the same.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to compounds of formula I:

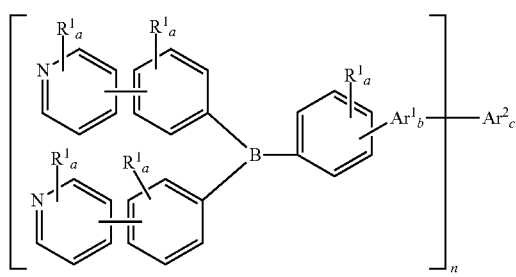

wherein
$R^1$ is, independently at each occurrence, a $C_1$-$C_{20}$ aliphatic radical, a $C_3$-$C_{20}$ aromatic radical, or a $C_3$-$C_{20}$ cycloaliphatic radical;
a is, independently at each occurrence, an integer ranging from 0-4;
b is 0, 1 or 2;
$Ar^1$ is a direct bond or heteroaryl, aryl, or alkyl or cycloalkyl;
$Ar^2$ is heteroaryl, aryl, or alkyl or cycloalkyl;
c is an integer ranging from 1-7; and
n is an integer ranging from 2-4.

In another aspect, the invention relates to optoelectronic devices comprising at least one compound of formula I, particularly where the compound is present in an electron-transporting layer.

DETAILED DESCRIPTION

Compounds of formula I have properties useful in optoelectronic devices, e.g., organic light emitting devices (OLEDs), and are particularly well suited for use in electron-transporting layers thereof.

In one aspect, the present invention relates to compounds of formula II

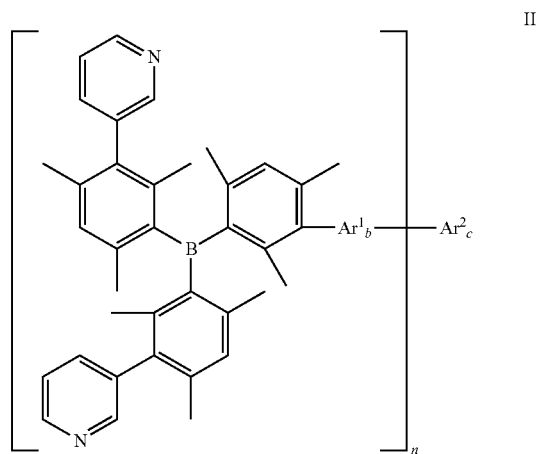

For the compounds of formula I and II, $Ar^1$ may be chosen from a direct bond and

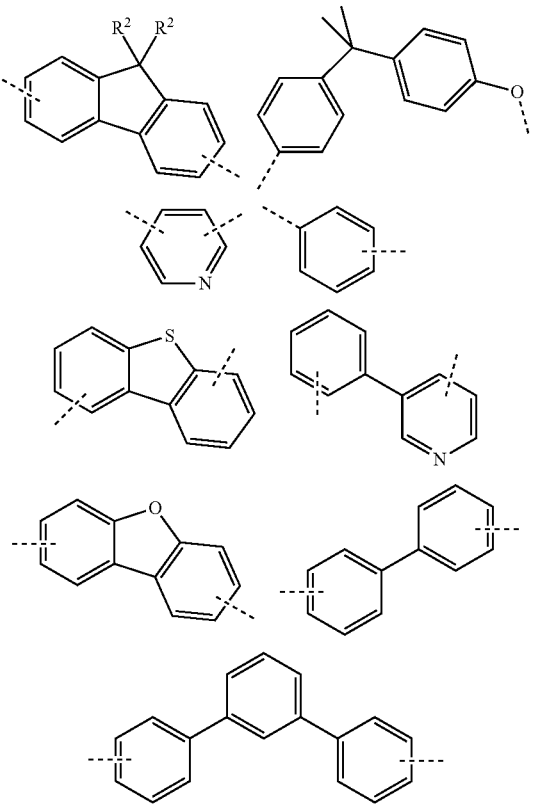

-continued
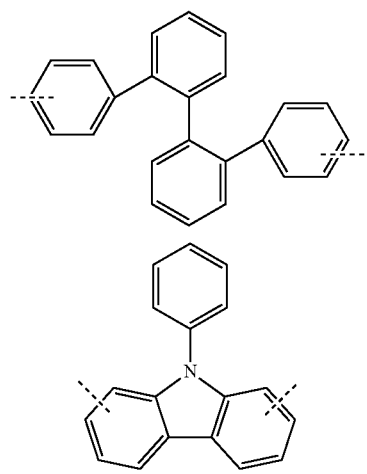
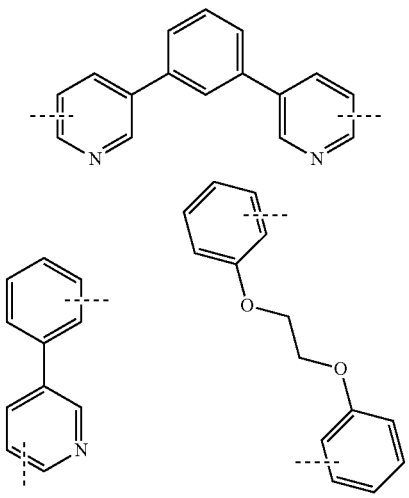
$R^2$ is, independently at each occurrence, a $C_1$-$C_{20}$ aliphatic radical, a $C_3$-$C_{20}$ aromatic radical, a $C_3$-$C_{20}$ cycloaliphatic radical, an aryl group or a heteroaryl group.
Examples of groups that may be used as $Ar^2$ include
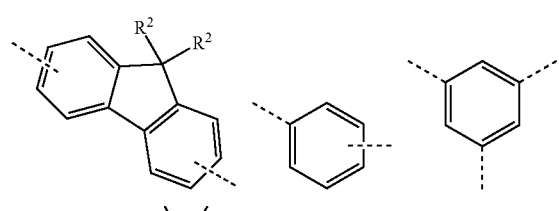
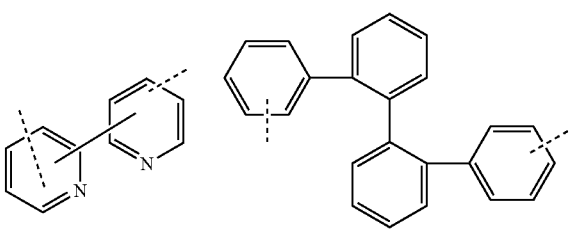
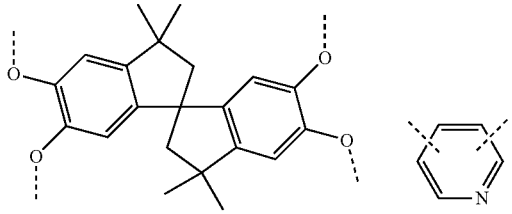
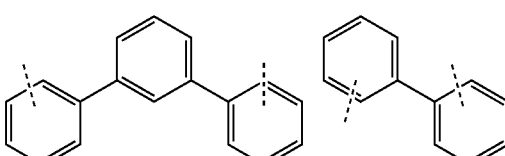
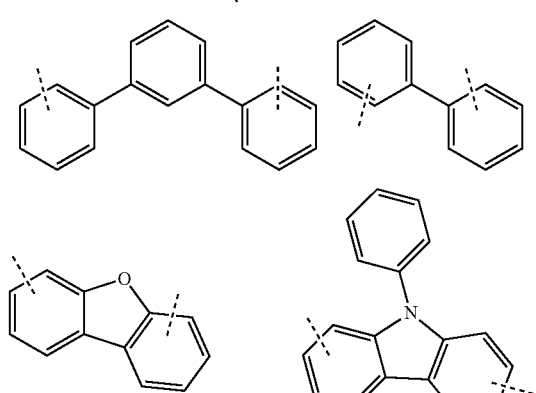
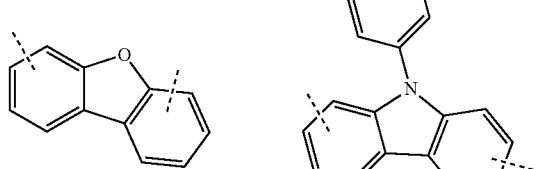
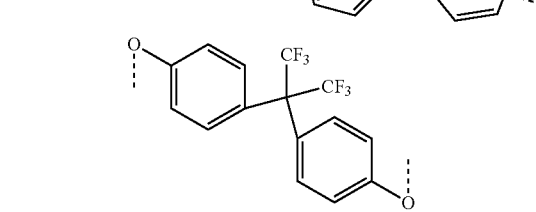
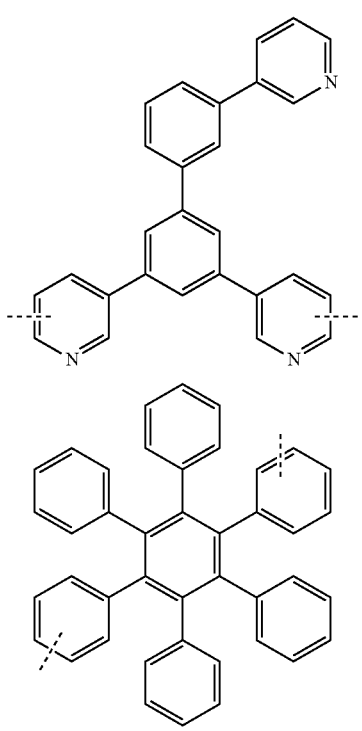

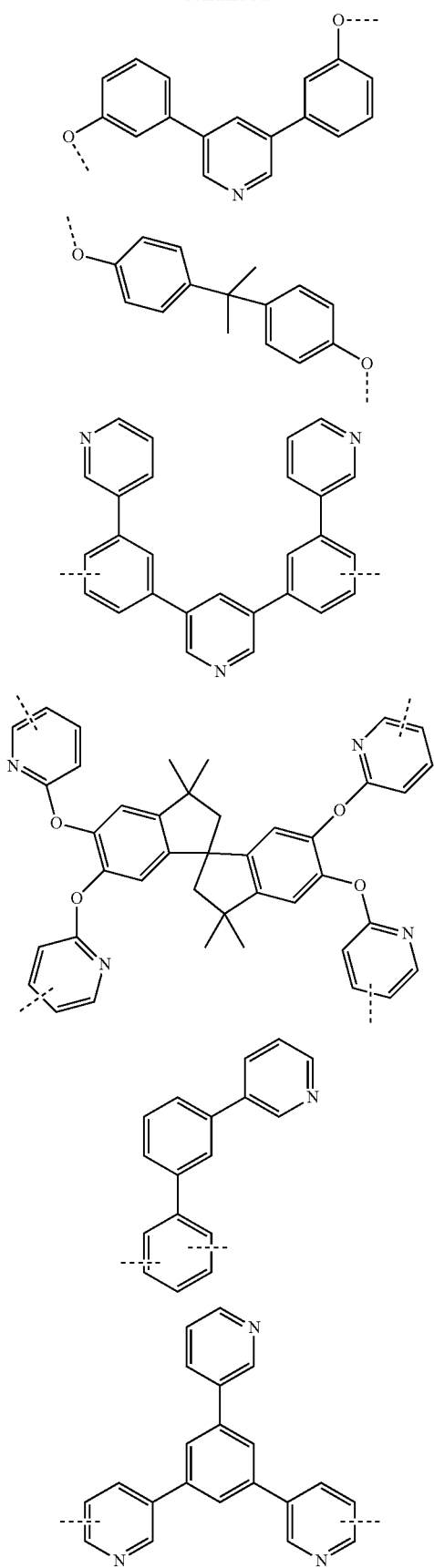
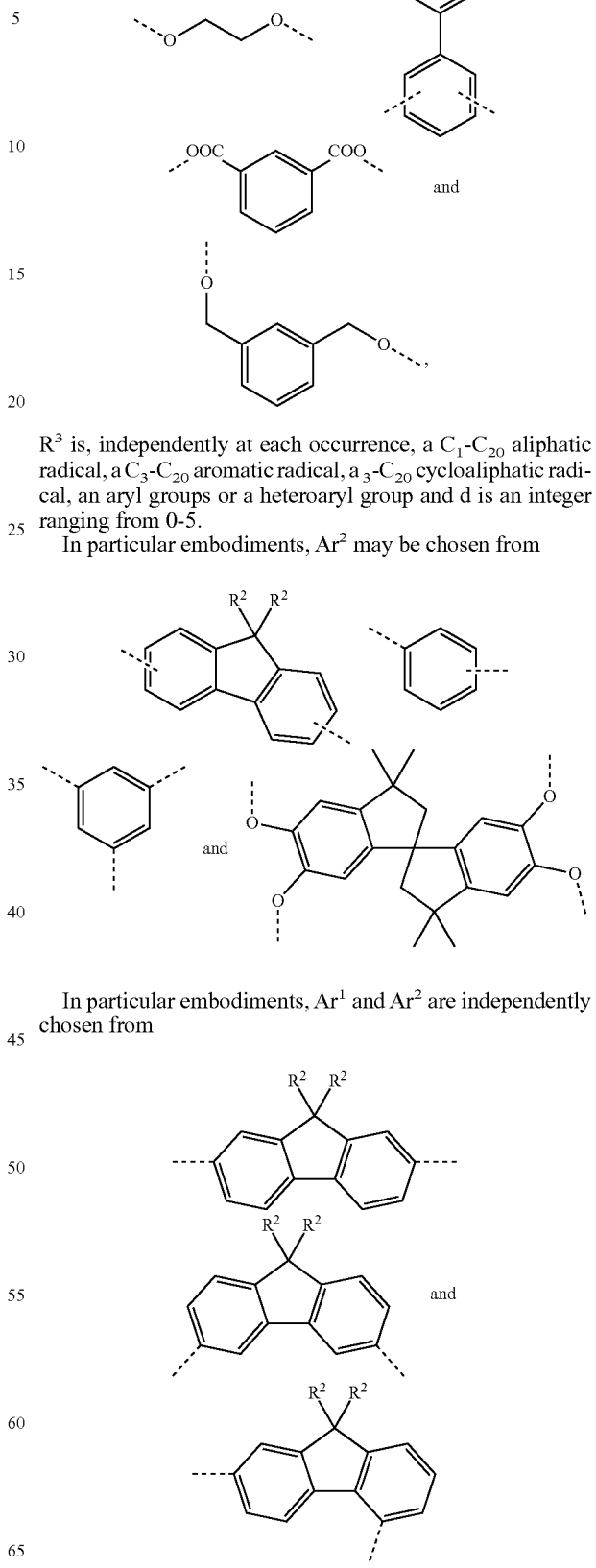
$R^3$ is, independently at each occurrence, a $C_1$-$C_{20}$ aliphatic radical, a $C_3$-$C_{20}$ aromatic radical, a $C_3$-$C_{20}$ cycloaliphatic radical, an aryl groups or a heteroaryl group and d is an integer ranging from 0-5.
In particular embodiments, $Ar^2$ may be chosen from
In particular embodiments, $Ar^1$ and $Ar^2$ are independently chosen from In some embodiments, $Ar^1$ and $Ar^2$ are independently chosen from

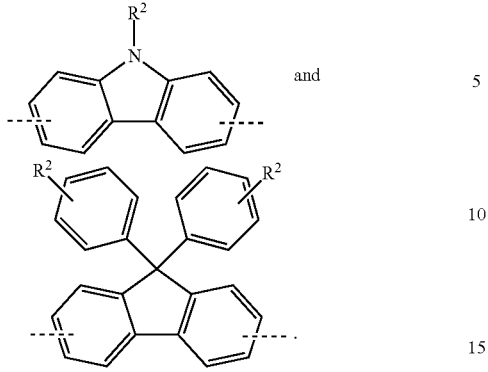

In one aspect, the compound of formula I is

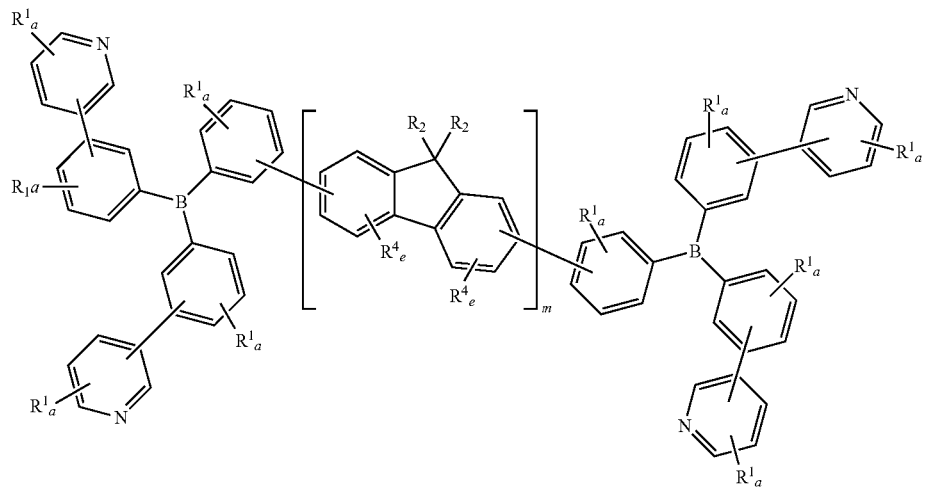

wherein
$R^4$ is, independently at each occurrence, a $C_1$-$C_{20}$ aliphatic radical, a $C_3$-$C_{20}$ aromatic radical, a $C_3$-$C_{20}$ cycloaliphatic radical, an aryl groups or a heteroaryl group and e is an integer ranging from 0-3; and
m is an integer ranging from 1-7.

In another aspect, the compound of formula I is

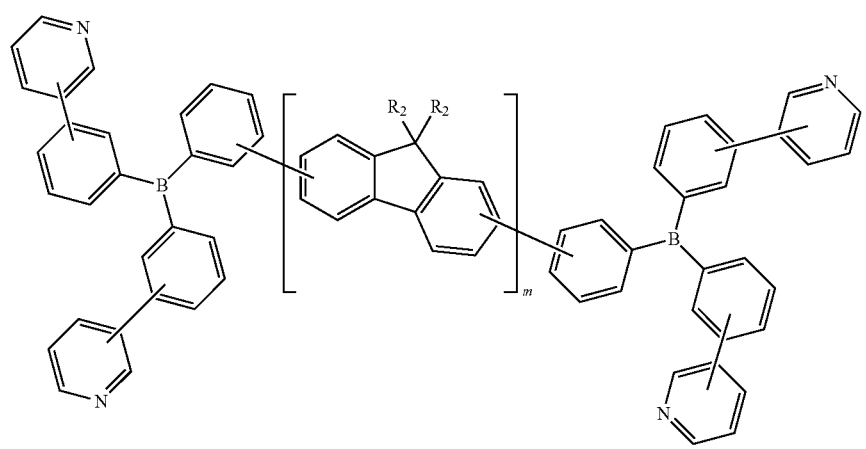

In another aspect, the compound of formula I is
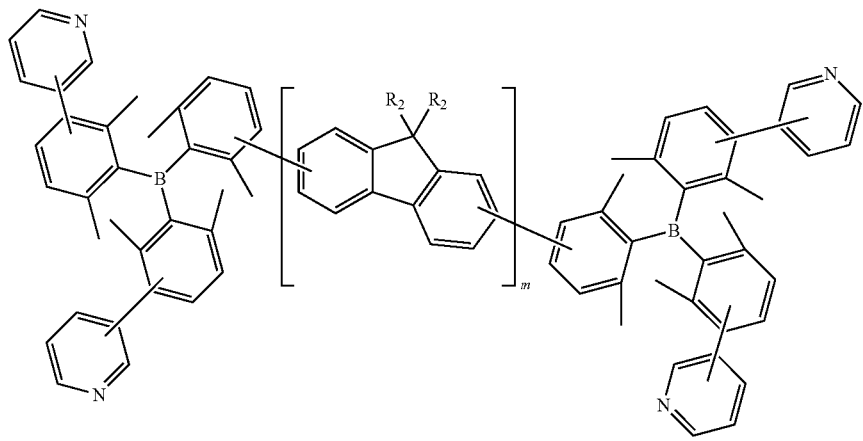
In particular embodiments, the compound is
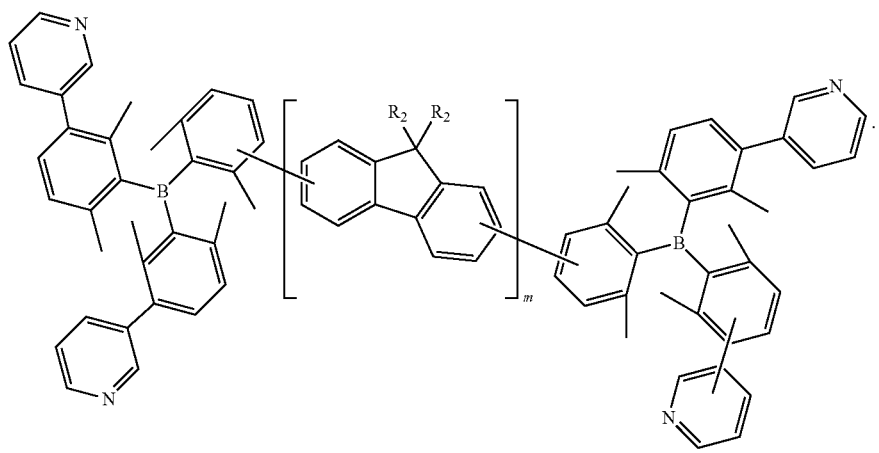
In yet another aspect, the compound is
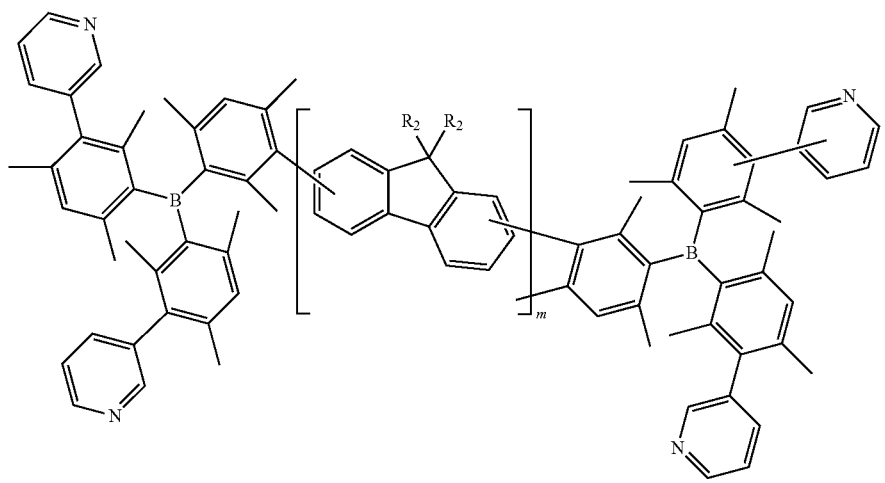

Examples of compounds include
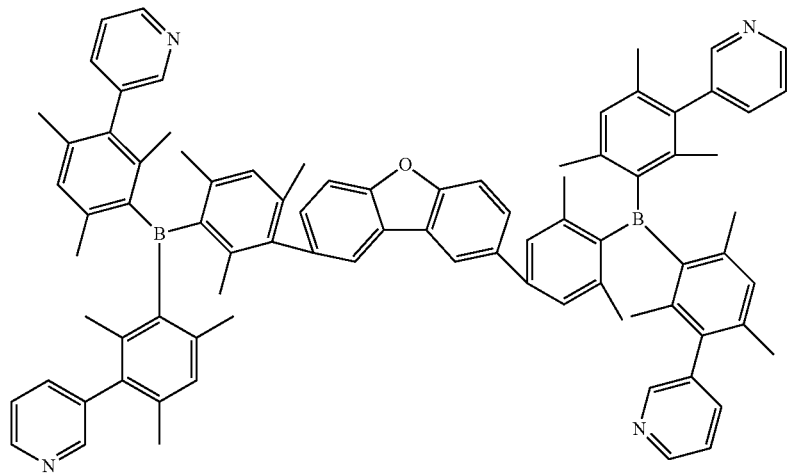
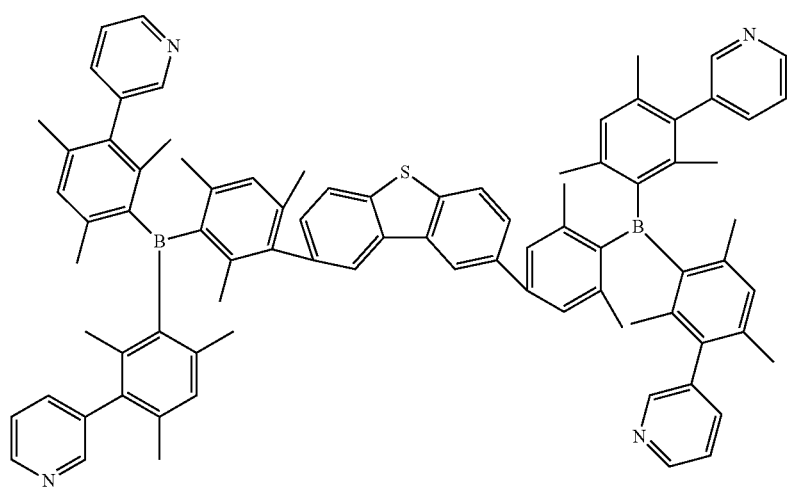
In particular embodiments, the compounds of formula I are chosen from
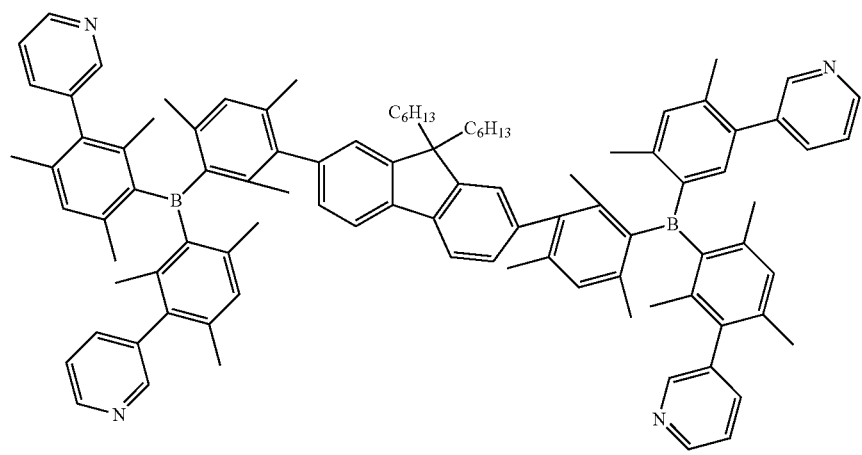

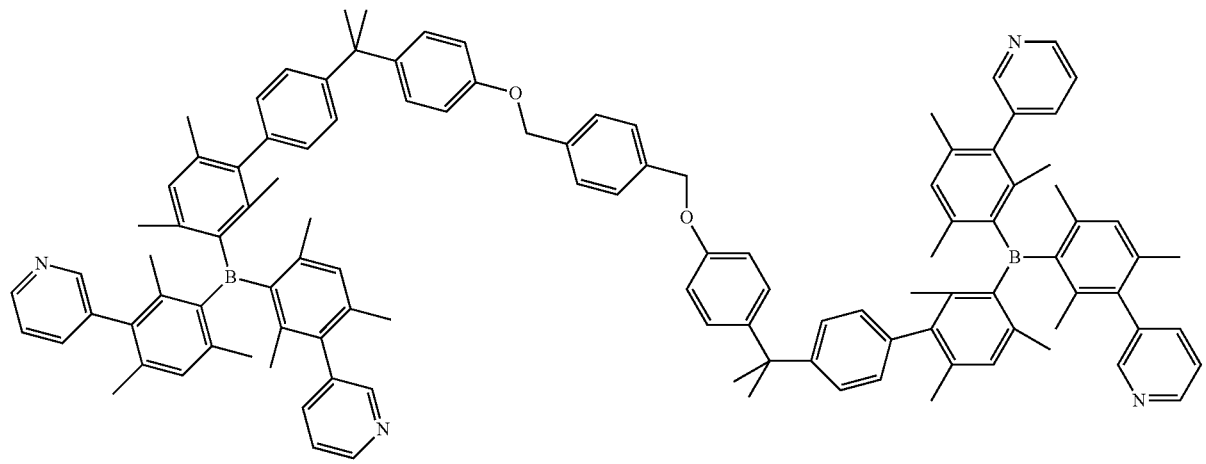
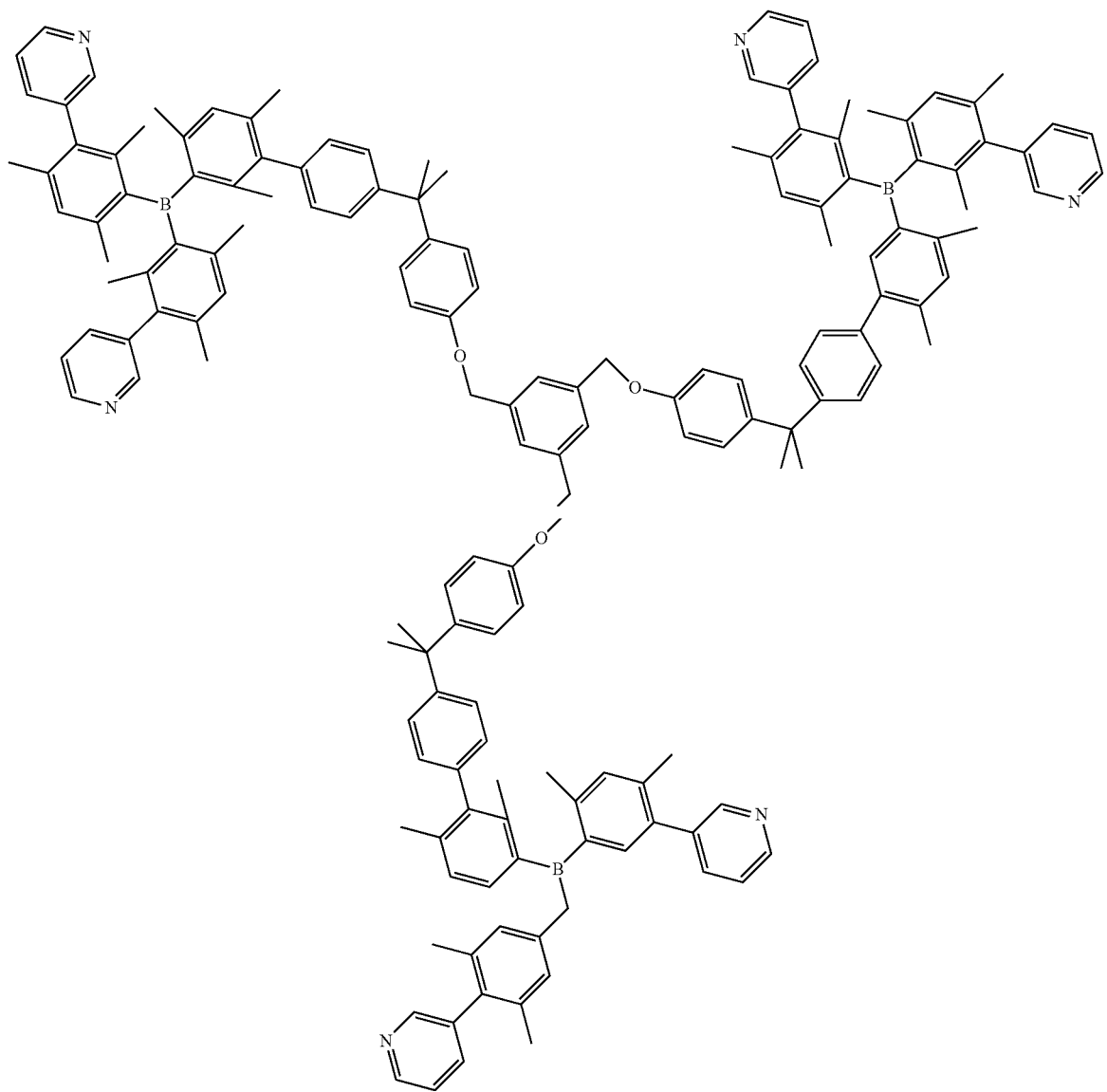

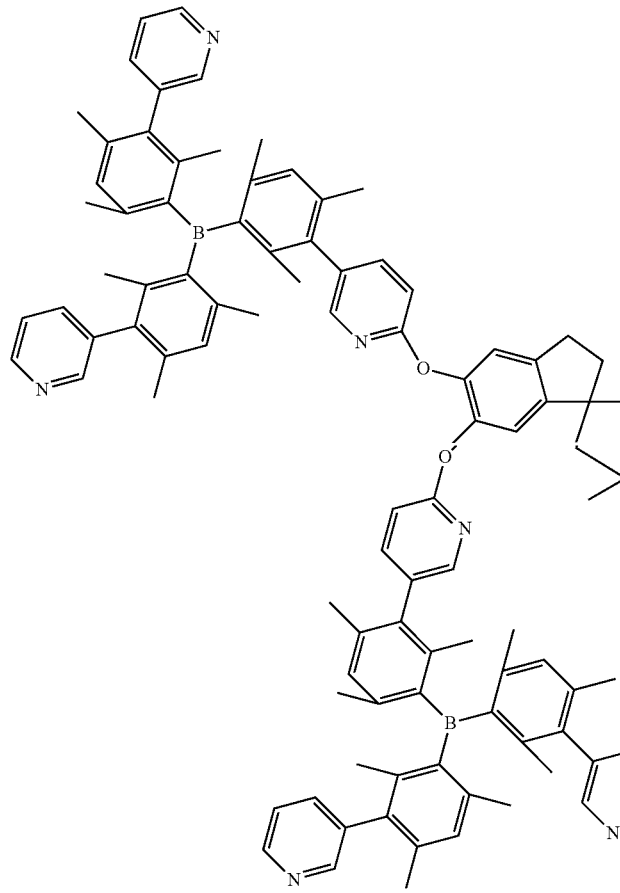
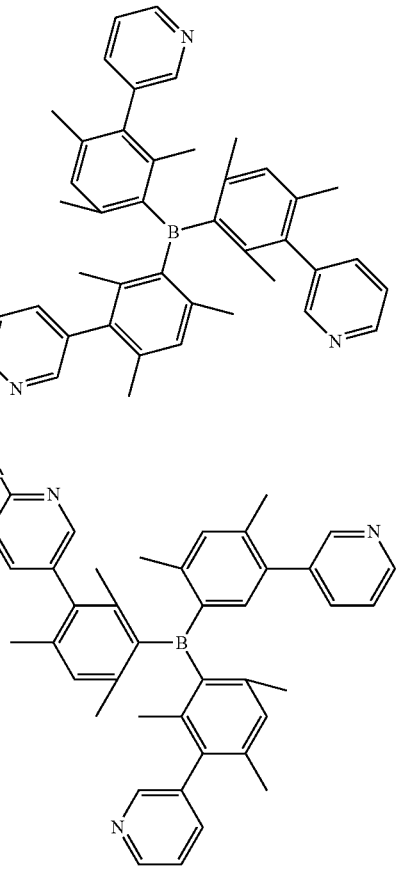

Aromatic boron compounds, including those of formula I and II, may be unstable in the presence of air and/or water. It has been reported that compounds having substituents adjacent to the boron atom exhibited enhanced stability under these conditions (JACS, vol. 120, page 10776 (1998)). Therefore, in some cases, it may be desirable to use compounds of formula I and II that have a substituent in one or both positions ortho- to the boron atom. The ortho-substituent may be any aromatic, aliphatic or cycloaliphatic radical, particularly an alkyl group, and more particularly a methyl group.

Durability of devices of the present invention may be affected by the manner in which pyridyl groups of the phenylpyridyl groups are attached to the phenyl ring. In some cases, durability of the device may be improved when the pyridyl group is attached at a position meta to the nitrogen atom.

The compounds of formula I and II may be prepared by employing Suzuki cross-coupling reactions. The general procedure for Suzuki cross-coupling reactions includes mixing an aryl halide and aryl borate (or boronic acid) in a suitable solvent, in the presence of a base and Pd catalyst. The reaction mixture is heated under an inert atmosphere for a period of time. Suitable solvents include but are not limited to Dioxane, THF, EtOH, toluene and mixtures thereof. Exemplary bases include $Na_2CO_3$, $K_2CO_3$, $Cs_2CO_3$, Potassium phosphate and hydrates thereof. The bases can be added to the reaction as a solid powder or as an aqueous solution. The most commonly used catalysts include $Pd(PPh_3)_4$, or $Pd(OAc)_2$, $Pd(dba)_2$ with the addition of a secondary ligand. Exemplary ligands include dialkylphosphinobiphenyl ligands, such as structures III-VII shown below, in which Cy is cyclohexyl.

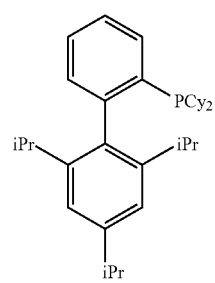

III

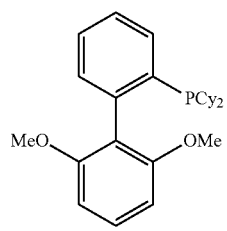

IV

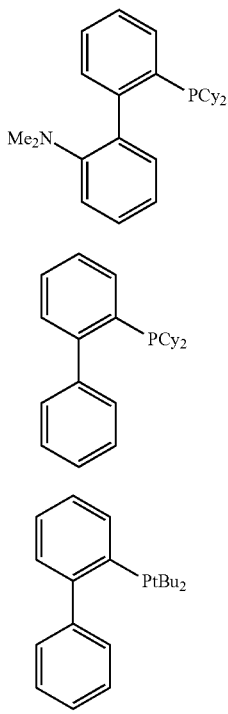

In general there are at least two methods that may be used to convert an aryl halide into its corresponding aryl borate. One method involves the generation of a carbanion either by using BuLi to effect a lithio-halogen exchange or by using Mg to generate a Grignard reagent, followed by quenching of the carbanion with a borate such as trimethylborate, triethylborate or tri(isopropyl)borate and the like. A typical procedure involves combining the starting materials in dry solvents such as THF or diethylether under anhydrous and inert conditions. The reaction is cooled to −100° C. or −80° C. and BuLi is added dropwise and stirred at this temperature for a certain amount of time (1-5 hours). After which time the intermediate carbanion is quenched with a suitable borate ester. The reaction mixture is allowed to warm to room temperature (RT), and, after stirring for 30 minutes at RT, the mixture is treated with a solution of saturated NH$_4$Cl (0.5 mL) and concentrated to dryness to afford a crude product.

The second method employs Pd-catalyzed borylation. A typical procedure includes combining an aryl halide and pinacolate diborane, anhydrous base and a dialkylphosphinobiphenyl ligand under dry and inert atmospheric conditions. The flask is protected from the atmosphere and charged with anhydrous solvent. After the solution is degassed for 15-30 minutes, the reaction mixture is charged with Pd catalyst and heated at reflux for an extended period by monitoring the disappearance of the starting aryl halide. Afterwards, the reaction mixture is cooled to RT and filtered. Upon concentration, the crude reaction product is afforded. Exemplary anhydrous bases include NaHCO$_3$, KHCO$_3$, and KOAc, particularly KOAc. Exemplary ligands include dialkylphosphinobiphenyl ligands, such as structures III-VII and trans-dichlorobis(triphenylphosphine)palladium (II).

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole locking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the compounds of the invention may be a fluorescent OLED comprising a singlet emitter. In another embodiment, the OLEDs comprising the compounds of the invention may be a phosphorescent OLED comprising at least one triplet emitter. In another embodiment, the OLEDs comprising the compounds of the invention comprise at least one singlet emitter and at least one triplet emitter. The OLEDs comprising the compounds of the invention may contain one or more, any or a combination of blue, yellow, orange, red phosphorescent dyes, including complexes of transition metals such as Ir, Os and Pt. In particular, electrophosphorescent and electrofluorescent metal complexes, such as those supplied by American Dye Source, Inc., Quebec, Canada may be used. Compounds of the formula I and II may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk resistivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode 20 include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Compounds of formula I and II may be used in electron transport layers in place of, or in addition to traditional materials such as poly(9,9-dioctyl fluorene), tris(8-hydroxyquinolato) aluminum ($Alq_3$), 2,9-dimethyl-4,7-diphenyl-1,1-phenanthroline, 4,7-diphenyl-1,10-phenanthroline, 2-(4-biphenylyl)-5-(4t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino) phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino) benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371. Compounds of formula I and II may be added into and/or in place of the above mentioned materials.

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine) (F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine) iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Compounds of formula I and II may form part of the electron transport layer or electron injection layer or light emissive layer. Thus, in one aspect, the present invention relates to more efficient optoelectronic devices, e.g., OLEDs comprising compounds of formula I and II. The OLEDs may be phosphorescent containing one or more, any or a combination of, blue, yellow, orange, red phosphorescent dyes.

Definitions

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having $4n+2$ "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph—), 4-(3-bromoprop-1-yl)phen-1-yl (i.e., 4-$BrCH_2CH_2CH_2$Ph—), and the like. Further examples of aromatic radicals include 4-allyloxyphen-1-oxy, 4-aminophen-1-yl (i.e., 4-$H_2$NPh—), 3-aminocarbonylphen-1-yl (i.e., $NH_2$COPh—), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh($CH_2$)$_6$PhO—), 4-hydroxymethylphen-1-yl (i.e., 4-$HOCH_2$Ph—), 4-mercaptomethylphen-1-yl (i.e., 4-HSCH$_2$Ph—), 4-methylthiophen-1-yl (i.e., 4-CH$_3$SPh—), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl (C$_3$H$_2$N$_2$—) represents a $C_3$ aromatic radical. The benzyl radical (C$_7$H$_7$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis (cyclohex-4-yl) (i.e., —C$_6$H$_{10}$C(CF$_3$)$_2$C$_6$H$_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy (2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g. (CH$_3$O)$_3$SiCH$_2$CH$_2$C$_6$H$_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a $C_4$ cycloaliphatic radical. The cyclohexylmethyl radical (C$_6$H$_{11}$CH$_2$—) represents a $C_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e. —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a $C_1$-$C_{10}$ aliphatic radical contains at least one but no more than 10 carbon atoms. A methyl group (i.e., CH$_3$—) is an example of a $C_1$ aliphatic radical. A decyl group (i.e., CH$_3$(CH2)$_9$—) is an example of a $C_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. As used herein, rings such as thiophene, pyridine, isoxazole, pyrazole, pyrrole, furan, etc. or benzo-fused analogues of these rings are defined by the term "heteroaryl."

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-11 describe the syntheses of compounds of the invention and intermediates used in making them. All reagents were purchased from Aldrich Chemical Co., Milwaukee, Wis., USA and Acros Organics unless other wise specified and were used without further purification. All compounds were characterized by $^1$H-NMR and found to correspond to the structures shown.

Example 1

Synthesis of Compound 1

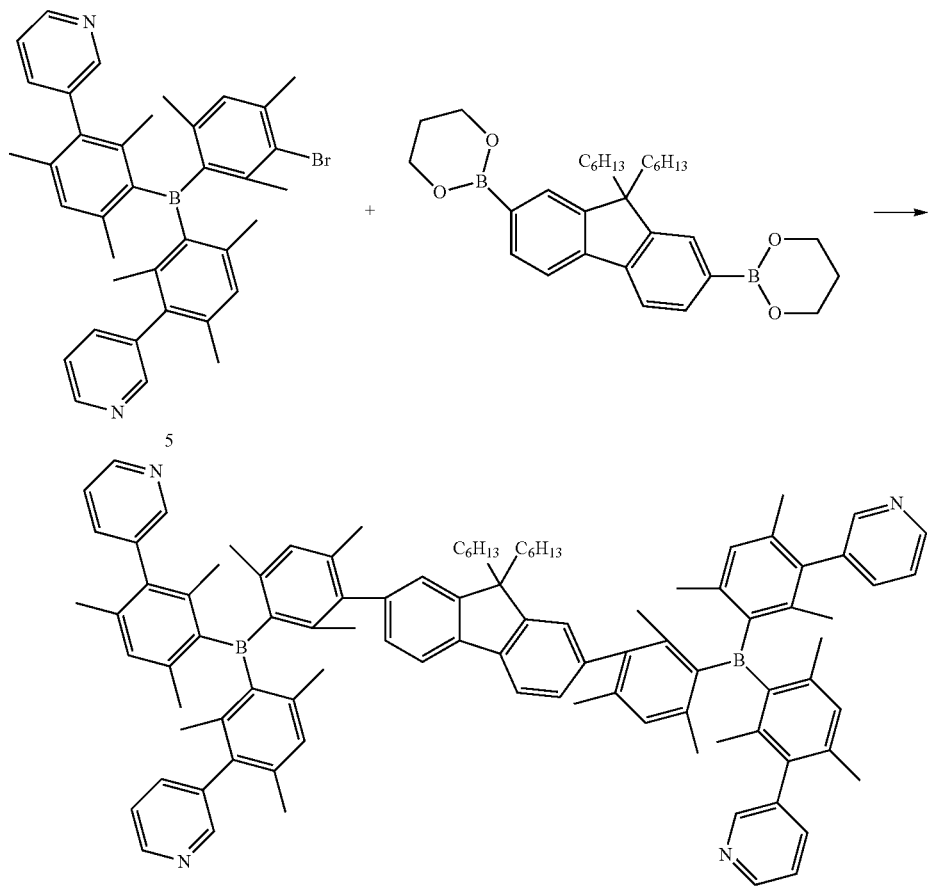

A 50 mL of three neck round bottom flask was charged with 0.6 g (1 mmol) of compound 5 (exact mass: 600.23), 0.2511 g (0.4998 mmol, 97% purity) of 9,9-dihexylfluorene-2,7-bis(trimethylene-borate) (exact mass: 502.34), 10.2 mg (0.045 mmol) of Pd(OAc)$_2$, 66 mg (0.16 mmol) of 2-dicyclohexylphosphino-2',6'-dimethoxy biphenyl (recrystalized from acetone before use), 11.1 g (15 mmol) tetraethyl ammonium hydroxide in water (20 wt % solution), and toluene 35 mL. The mixture was degassed and purged with Ar three times. Stirring and heating started and continued at 75° C. for 48 hours, while the flask was kept under Ar atmosphere. Then the solution was allowed to cool to room temperature, water (20 mL) was added. Organic layer was separated and aqueous phase was discarded. Organic phase was washed with water (30 mL×2) and brine (30 mL×1) and dried over Na$_2$SO$_4$. Then the solution was concentrated and purified using a Teledyne Isco COMBIFLASH® liquid chromatography system, using 40 g of silica gel column, ethylacetate/hexane 80-100% eluting solvent. This process was repeated three times to get the final product (exact mass: 1374.88). $^1$H NMR (CDCl$_3$): 8.57 (broad doublet, 4H), 8.35 (m, 4H), 7.71 (broad triplet, 2H), 7.48 and 7.37 (broad multiplet, 8H), 6.95 (broad multiplet, 10H), 1.98 (multiplets, 58H), 1.0 (broad, 12H), 0.76(t, 2H), 0.66 (broad multiplet, 8H). Maldi (M+=1375.7616).

Example 2

Synthesis of Compound 5

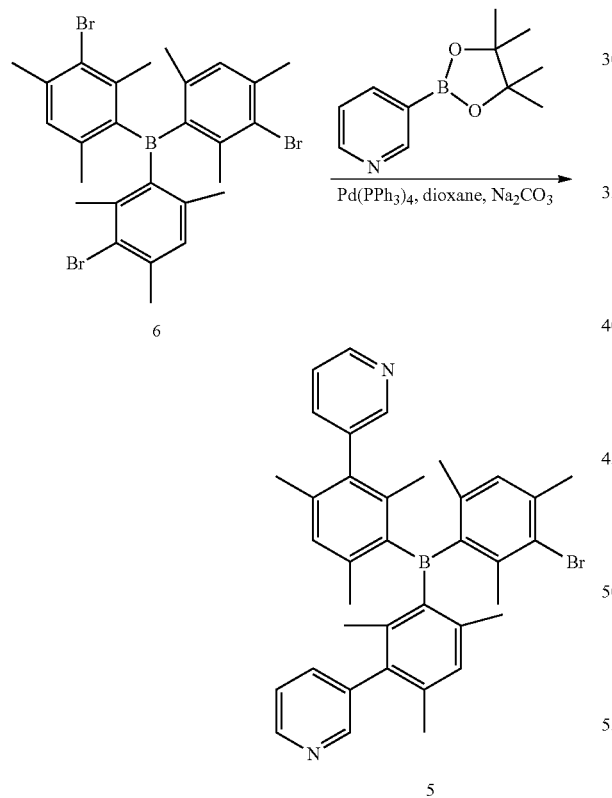

Tris(bromomesityl) borane (6) (11.1 g., 18.4 mmol) and 7.57 g of 3-pyridylboronic acid pinacol ester (36.9 mmol) and was added into 50 mL of dioxane along with 20 mL of Na$_2$CO$_3$ solution (2N) in a flask. The flask was evacuated and purged with argon three times. Then 160 mg of Pd(PPh$_3$)$_4$ was added and the flask was evacuated and purged with argon three times. The reaction mixture was heated at 90° C. for 48 hours. After the reaction was cooled to room temperature, dioxane was removed by rotoevaporation. The residue was re-dissolved in CH$_2$Cl$_2$ (50 mL) and extracted with water (50 mL×2), brine (50 mL) and dried over anhydrous MgSO$_4$, and concentrated under reduced pressure. The crude product was further purified on silica gel using EtOAc/Hex (0-100%) as eluting solvent. At 35%, 60% and 100% EtOAc, mono, di, tri adduct were collected respectively. $^1$H NMR for di-substituted product $^1$H (CDCl3, RT) 8.56 (m, 2H), 8.34 (m, 2H), 7.45 (m, 2H), 7.34 (m, 2H), 6.90 (m, 3H), 2.4-1.62 (multiple multiplet, 27H).

Example 3

Synthesis of Compound 6

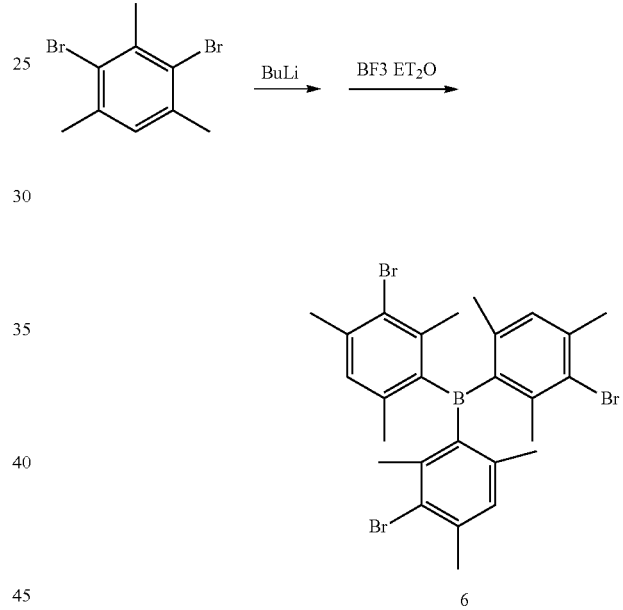

To a solution of 2,4-dibromomesitylene (13.9 g, 50 mmol) in dry Et$_2$O (400 mL) was added drop wise a hexane solution of n-BuLi (1.6 M, 31.25 mL, 50 mmol) at −78° C. The reaction mixture was allowed to warm to 0° C. and stirred for 20 min. To the mixture was added BF$_3$.OEt$_2$ (2.0 mL, 15.8 mmol) at −78° C. The reaction mixture was warmed up to room temperature over 1 h and stirred for overnight. After addition of water, the mixture was extracted with Et$_2$O. The extract was washed with brine, dried over anhydrous MgSO$_4$, and concentrated under reduced pressure to obtain a yellowish oil. The residue was dissolved in Et$_2$O and MeOH was added. Overnight, the solvent evaporated and crystals formed. The white crystals was collected by suction filtration and washed with MeOH to afford compound 6 (4.53 g, 47.7% yield). $^1$H (tetrachlorethane-d$_2$, 120° C.) 6.9 (s, 3H), 1.8 (s, 9H), 1.5 (s, 9H), 1.3 (s, 9H). $^1$H (tetrachlorethane-d$_2$, 30° C.), 6.9 (bs+s, 3H), 1.8 (s, 9H), 1.59 (d, 4.5H), 1.48 (d, 4.5H), 1.35 (d, 4.5H), 1.15 (d, 4.5H). $^{13}$C (tetrachlorethane-d$_2$, 120° C.) 146.2, 139.8, 139.7, 138.9, 131.0, 126.9, 24.4, 24.3, 24.4.

Example 4

Synthesis of Compound 2

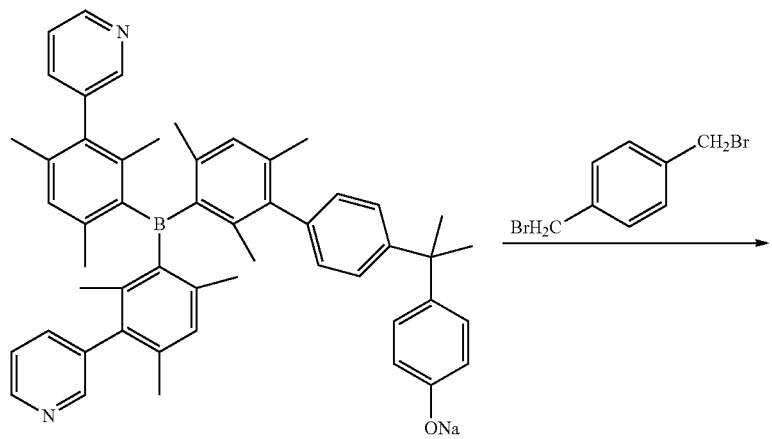

7

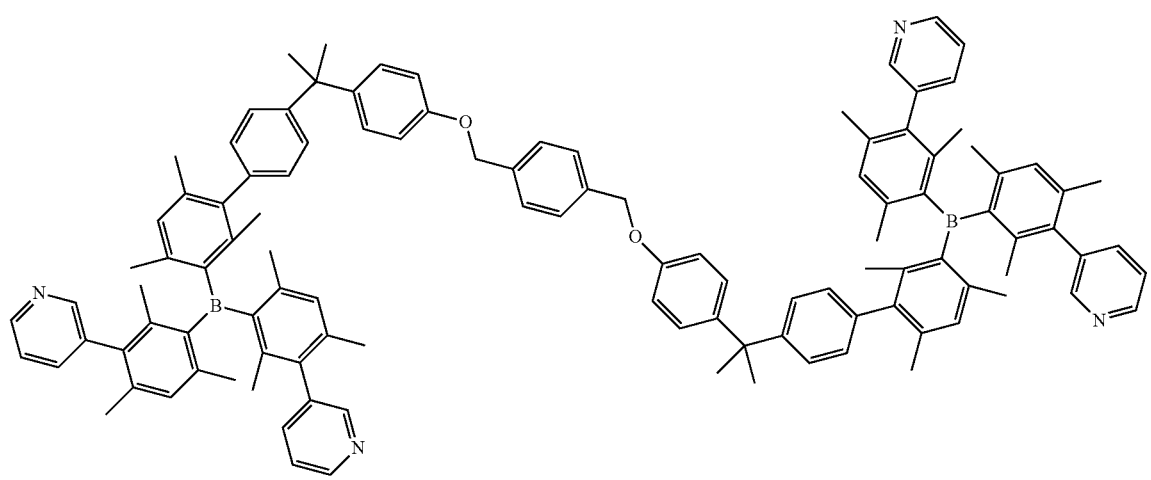

2

Dibromo-p-xylene was recrystalized from toluene before use. Compound 7 (0.2 g, 0.26 mmol) was dissolved in 15 mL of toluene and drying azeotropically. Then 0.0316 g (0.12 mmol) of dibromo-p-xylene was added, with a pinch of tetrabutyl ammonium iodide. Reaction was refluxed overnight. The second day, after cool, toluene was extracted with 10 mL of water and dried over $Na_2SO_4$. The crude product was afforded after roto-evaporation. The crude product was purified using a Teledyne Isco COMBIFLASH® liquid chromatography system, with 12 g of silica gel column, THF/hexane 30-100% eluting solvent to provide compound 2 (exact mass: 1566.90). $^1H$ (CDCl$_3$) δ 8.54 (dd, 4H), 8.39-8.24 (m, 4H), 7.51-7.41(broad m, 4H), 7.41-7.30 (broad m, 6H), 7.25-7.13

(m, 4H), 7.09 (t, 4H), 6.78 (t, 4H), 6.99-6.81 (10H), 5.06 (broad d, 4H), 2.16-1.90 (m, 42 H), 1.86-1.61 (m, 24H), Maldi (M+=1568.7839).

Example 5

Synthesis of Compound 7

δ 8.53 (broad doublet, 2H), 8.24 (broad m, 2H), 7.46 (m, 4H), 7.21 (m, 2H), 6.41 (m, 7H), 6.65 (t, 2H), 1.97 (m, 21 H), 1.68 (m, 12H).

Example 6

Synthesis of Compound 8

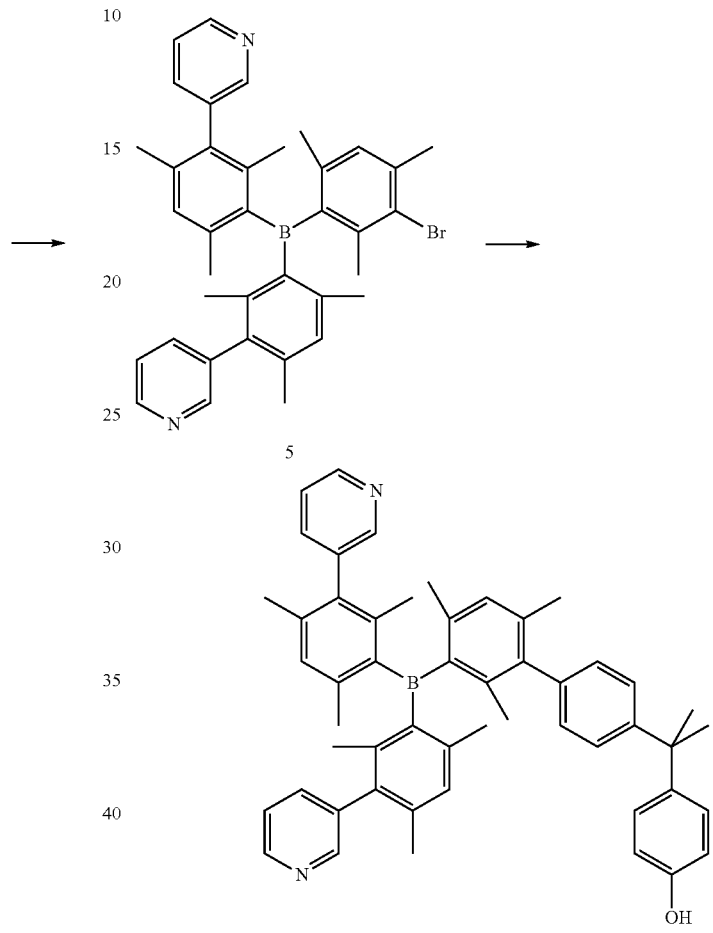

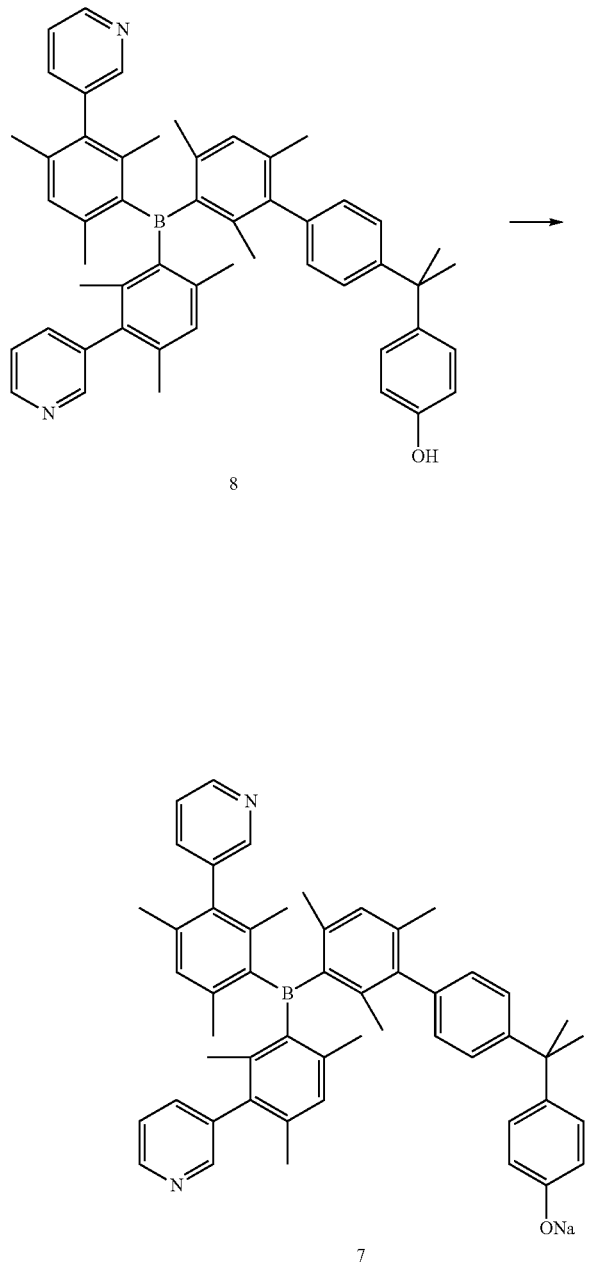

Compound 8 (0.53 g, 0.7236 mmol) was dissolved in methanol, and 1.39 mL of sodium methoxide in methanol (0.48-0.52 M) was added. After stirring at room temperature for 1 hour, a sample was taken, and analyzed by 1H in DMSO after removal of methanol using roto-evaporation. 0.18 uL of sodium methoxide in methanol solution was added. After stirring for another hour, the solution was evaporated and stored in a $N_2$ purged glove box for the next step. $^1$H (DMSO)

A 50 mL of three neck round bottom flask was charged with 3.08 g (4.97 mmol) of compound 5, 1.84 g of BPA boron ester (5.4 mmol), 8.4 mg (0.037 mmol) of Pd(OAc)$_2$, 54.56 mg (0.13 mmol) of 2-dicyclohexylphosphino-2',6'-dimethoxy biphenyl (recrystalized from acetone before use), 9.17 g (12.5 mmol) tetraethyl ammonium hydroxide in water (20 wt % solution), 9.17 g water and 50 mL toluene. The mixture was degassed and purged with Ar three times. Stirring and heating started and continued at 75° C. for 20 hours, while the flask was kept under Ar atmosphere. Then the solution was allowed to cool to room temperature, water (20 mL) was added. The organic layer was separated and the aqueous phase was discarded. Organic phase was washed with water (50 mL×2) and brine (50 mL×1) and dried over Na$_2$SO$_4$. Then the solution was concentrated and purified using a Teledyne Isco COMBIFLASH® liquid chromatography system using 120 g (×2) of silica gel column, ethylacetate/hexane 0-100% eluting solvent. $^1$H (DMSO) δ 9.20 (s, 1H, OH), 8.53 (broad doublet, 2H), 8.24 (broad m, 2H), 7.46 (m, 4H), 7.21 (m, 2H), 6.41 (m, 7H), 6.65 (t, 2H). 1.97 (m, 21 H), 1.68 (m, 12H).

Example 7
Synthesis of Compound 3
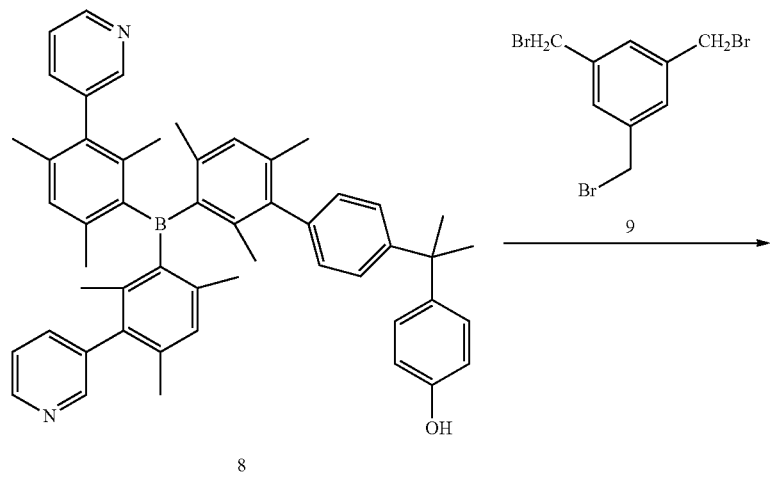

Compound 8 (0.5208 g, 0.7099 mmol) was added into 20 mL of THF along with 0.02 g of NaH (0.83 mmol). After stirring 1 hour at room temperature, 0.078 g (0.21 mmol) of tribromomesitylene was added. The reaction was refluxed over night under nitrogen. After concentration, the crude product was purified using a Teledyne Isco COMBIFLASH® liquid chromatography system, with 12 g of silica gel column, THF/hexane 30-100% eluting solvent. $^1$H (CDCl$_3$) δ 8.52 (d, 6H), 8.30 (m, 6H), 7.49-7.37 (broad m, 6H), 7.36-7.26 (broad m, 6H), 7.26-7.09 (broad m, 9H), 7.06 (t, 3H), 6.86 (broad m, 17.63 H), 6.70 (t, 2H), 5.03 (broad s, 6H), 2.16-1.90 (m, 63 H), 1.86-1.61 (m, 36H). Maldi (M$^+$=2312.5358)

Example 8

Synthesis of Compound 9

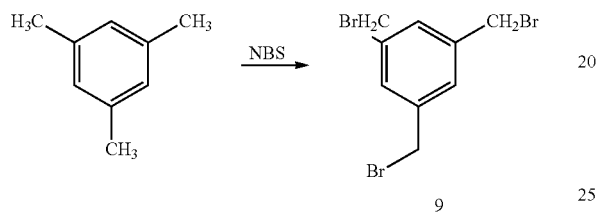

A solution containing 2 g (16.6 mmol) of mesitylene, 9 g (0.05 mol) of NBS, 0.088 g of benzoyl peroxide (BPO) and 50 mL of benzene was heated to reflux to initiate the reaction. The reaction was then refluxed overnight and allow to cool to room temperature. After filtering, the filtrate was washed with water and dried over Na$_2$SO$_4$. Concentration afforded the colorless crystals. This crude product was recrystalized from ethanol/hexane (1:1) twice, and 0.85 g of product was obtained. $^1$H (CDCl$_3$) δ 7.38 (s, 3H), 4.47 (s, 6H).

Example 9

Synthesis of Compound 4

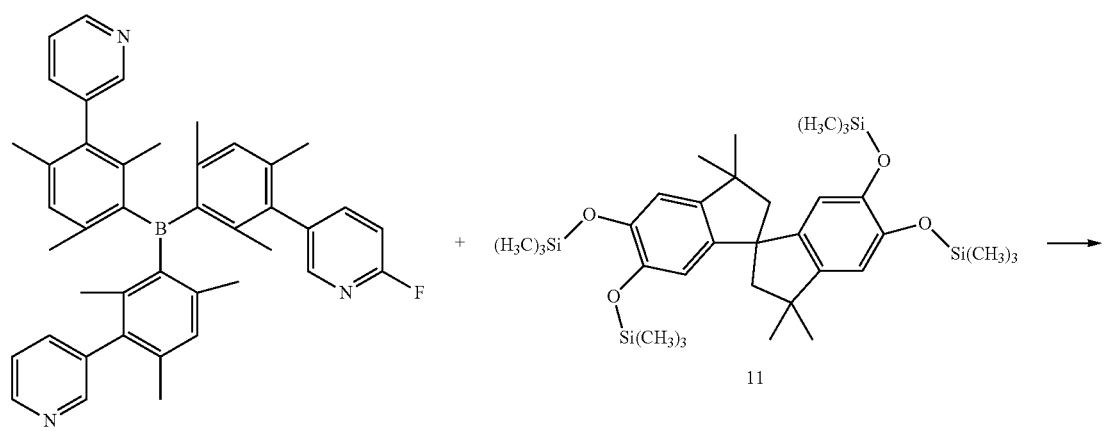

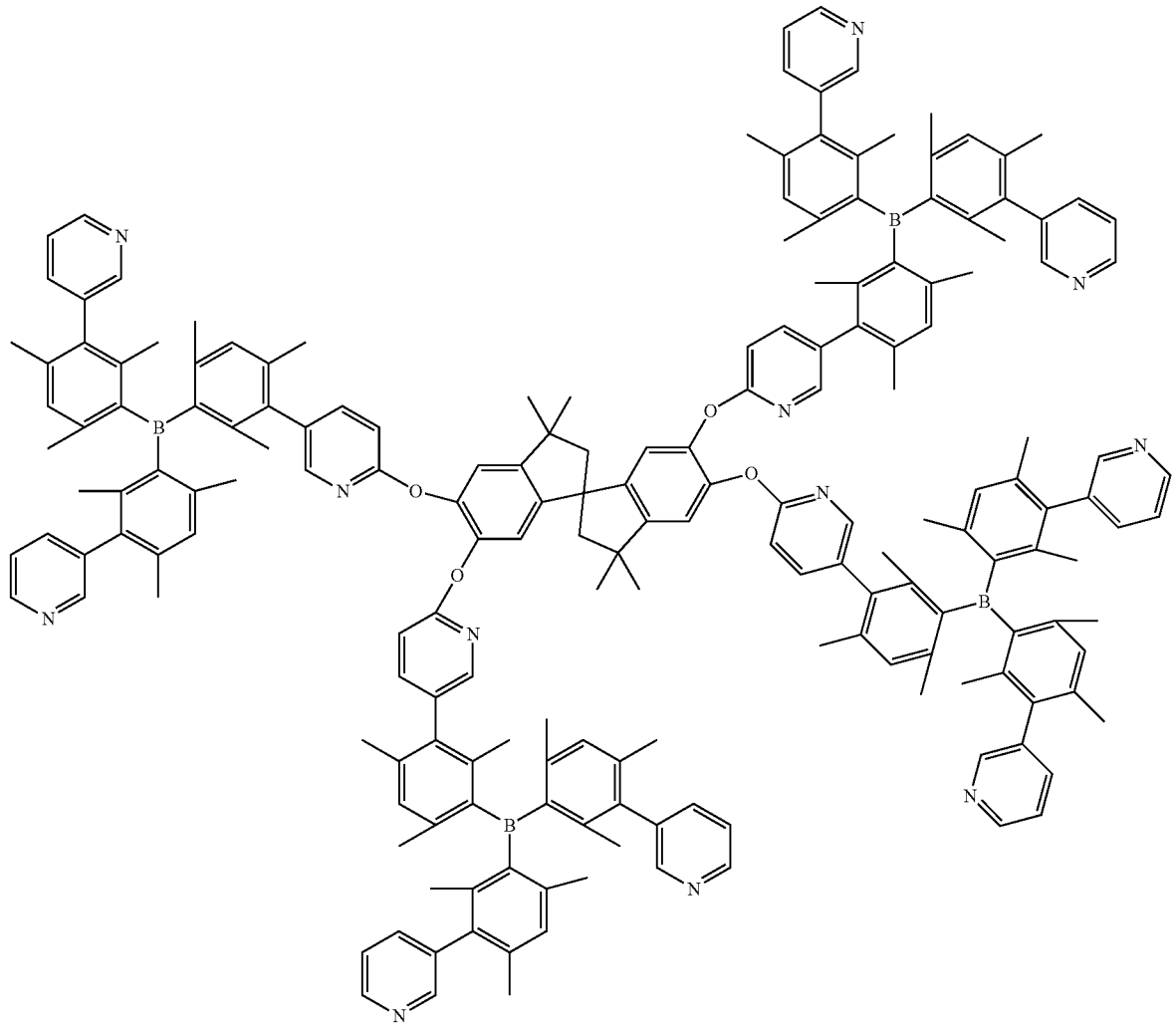

4

Compound 10 (0.80 g, 1.30 mmole, 6.9 eqv.) and 0.1185 g (0.1883 mmole, 1.0 eqv) of silylate tetraphenol was combined in a three neck round bottom flask at room temperature. To this flask, 10 mL of anhydrous DMF and 3 mL of anhydrous toluene was added. The flask was heated to 130° C. under a stream of argon. After toluene removal, then very small amount of anhydrous CsF (0.1 g) was added. The temperature was raised to 140° C. The reaction was monitored by silica gel TLC (THF/Hex=1/1-3/1). And the reaction was heated and stirred for two weeks. After the reaction mixture was cooled to room temperature, it was dumped into 10 mL of water. Methylene chloride (5 mL) was used to extract the solid. The organic layer was washed with water 5 mL (×2), brine 5 mL (×1), and dried over $MgSO_4$. The solvent was removed by a roto-evaporator. The crude product was separated by silica gel column using THF/Hex (1/1-6/1) as elute. About 0.25 g of a brownish solid was obtained. This product was purified multiple times using prep TLC and a solid (20 mg) of a slightly beige color was obtained (exact mass: 2729.49). $^1$H NMR (CDCl$_3$): 8.56 (broad s, 8H), 8.36 (broad s, 8H), 7.78 (broad s, 4H), 7.57-7.03 (broad m, 21H), 6.99-

6.54 (broad s, 1H), 3.93 (broad s, 4H), 2.42 (broad s, 4H), 2.37 (s, 12H), 2.23-1.55 (broad m, 92 H), 1.5-1.31 (broad m, 16H). Maldi ($M^+$=2729.5730)

Example 10

Synthesis of Compound 10

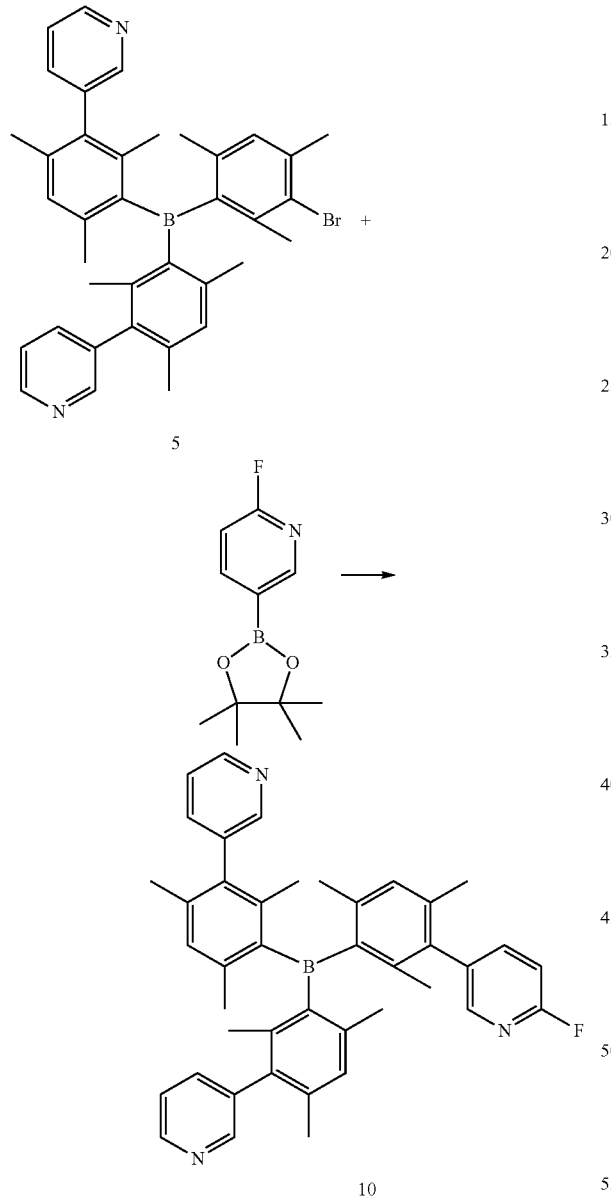

Bromomesityl-bis(3-pyridyl mesityl) borane (compound 5) (0.6 g, 1.0 mmol), 0.2899 g (1.3 mmol) of 2-fluoro-5-(4,4,5,5-tetramethyl-[1,3,2]-dioxaborolan-2-yl)-pyridine were combined in 5 mL dioxane, along with 2 mL of $Na_2CO_3$ (2M). The reaction vessel was degassed and purged with argon three times. $Pd(PPh_3)_4$ (3-5 mg) was added into solution, degassed and filled with argon again. The reaction was refluxed under argon at 90° C. for 48 hours. The dioxane was removed by roto-evaporation, and the resulting mixture was re-dissolved in $CH_2Cl_2$ (20 mL), extracted with water (20 mL×2) and brine (20 mL), and dried over $Na_2SO_4$. After concentration, the product was purified with 80 g of alumina column using a Teledyne Isco COMBIFLASH® liquid chromatography system, using hexane/ethyl acetate as the eluting solvent, afforded 0.46 g of product. $^1$H NMR ($CDCl_3$): 8.58 (d, 2H), 8.36 (d, 2H), 8.01-7.86 (m, 1H), 7.62-7.30 (m, 5H), 7.05-6.74 (t, t, d, 4H), 2.17-1.91 (m, 18H), 1.88-1.68 (m, 9H).

Example 11

Synthesis of Compound 11

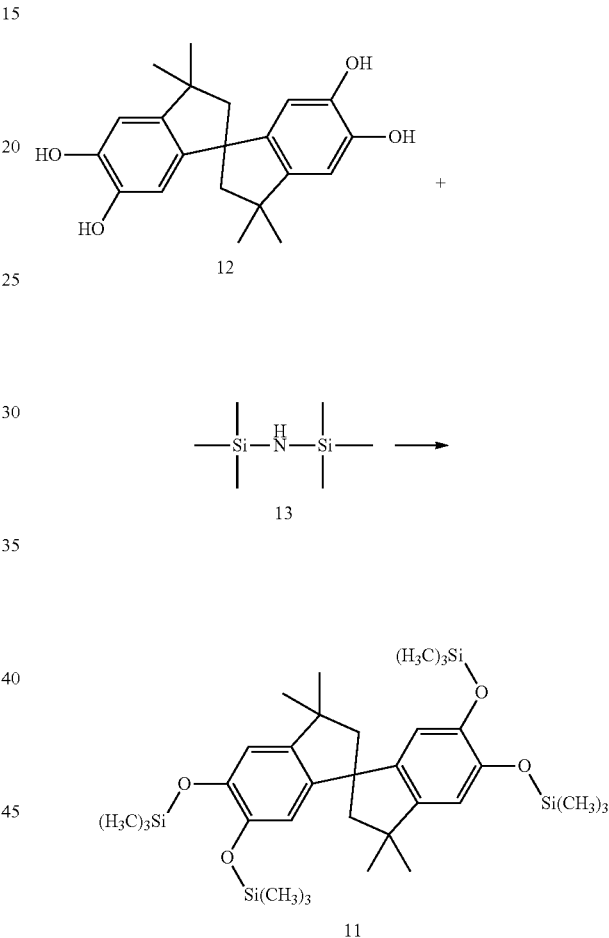

Spirobisindane tetraphenol (compound 12, 3.4 g, 10 mmol, exact mass: 340.17) was added into 4 g (24.8 mmol) of hexamethyldisilazane (compound 13, molecular weight: 161.39), and refluxed overnight at 120-125° C. It started out as a suspension and it turned into a clear solution after about 1 hour. The excess hexamethyldisilazane was removed by distillation to afford the final product. $^1$H NMR ($CDCl_3$): 6.6 (s, 2H), 6.2 (s, 2H), 2.2 (dd, 4H), 1.34 (s, 6H), 1.30 (s, 6H), 0.24 (s, 18H), 0.18 (s, 18H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:
1. A compound of formula I

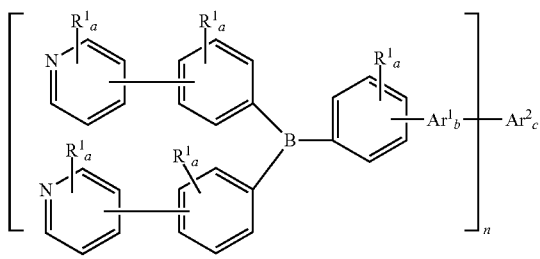

wherein
  $R^1$ is, independently at each occurrence, a $C_1$-$C_{20}$ aliphatic radical, a $C_3$-$C_{20}$ aromatic radical, or a $C_3$-$C_{20}$ cycloaliphatic radical;
  a is, independently at each occurrence, an integer ranging from 0-4;
  b is 0, 1 or 2;
  $Ar^1$ is a direct bond or heteroaryl, aryl, or alkyl or cycloalkyl;
  $Ar^2$ is heteroaryl, aryl, or alkyl or cycloalkyl;
  c is an integer ranging from 1-7; and
  n is an integer ranging from 2-4.

2. The compound according to claim 1, being of formula

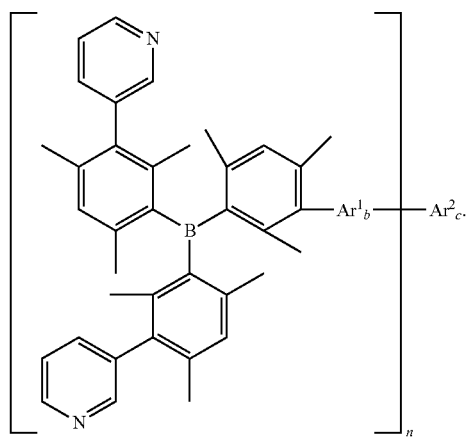

3. The compound according to claim 1, wherein $Ar^1$ is a direct bond.

4. The compound according to claim 1, wherein $Ar^1$ is chosen from

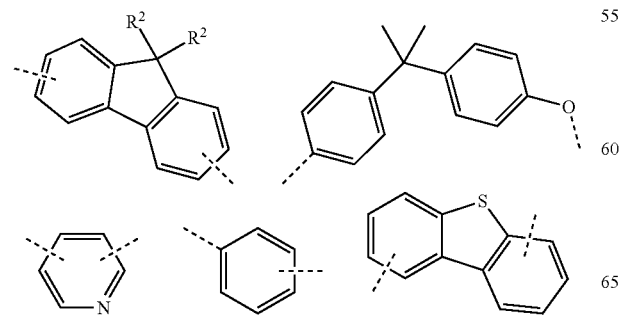

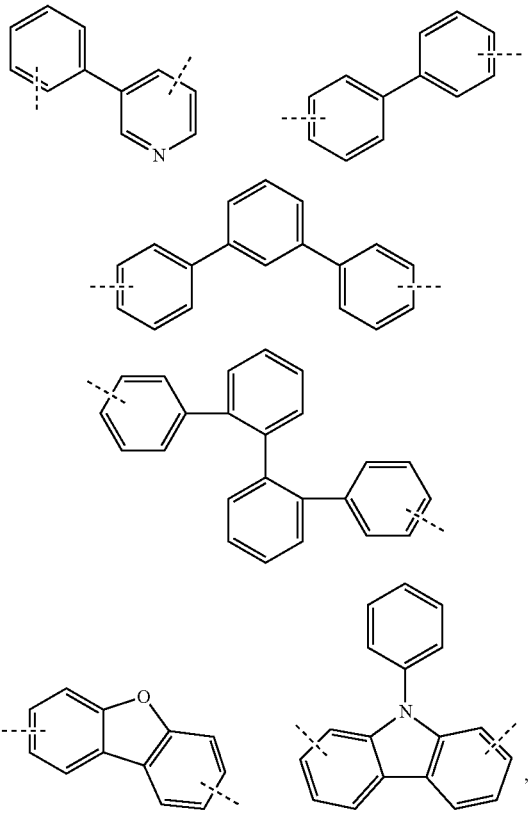

$R^2$ is, independently at each occurrence, a $C_1$-$C_{20}$ aliphatic radical, a $C_3$-$C_{20}$ aromatic radical, a $C_3$-$C_{20}$ cycloaliphatic radical, an aryl groups or a heteroaryl group.

5. The compound according to claim 1, wherein $Ar^2$ is chosen from

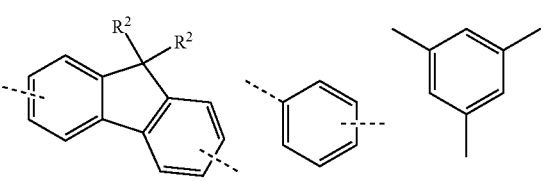

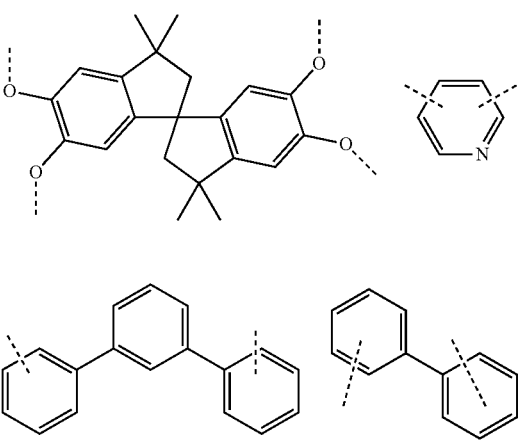

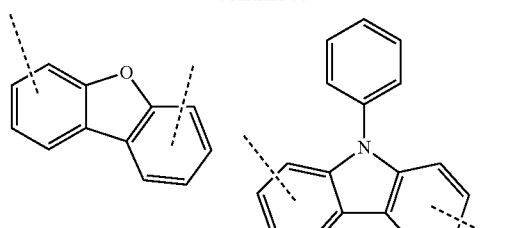
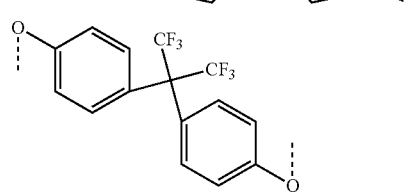
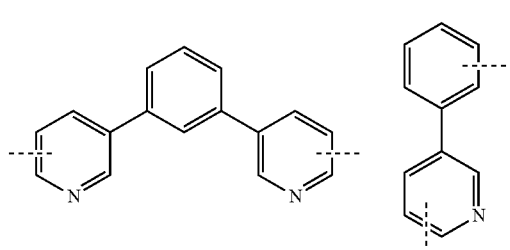
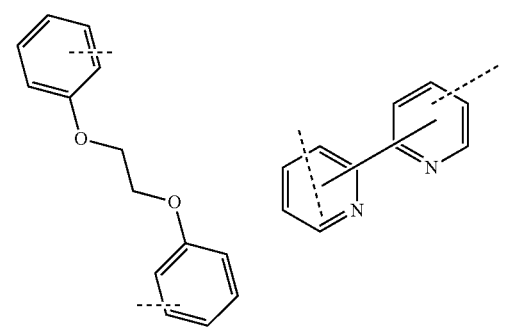
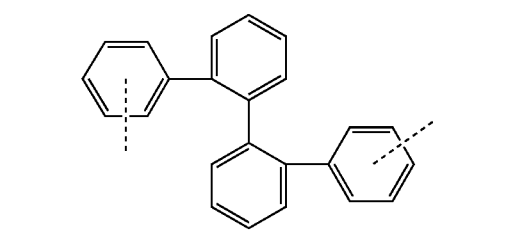
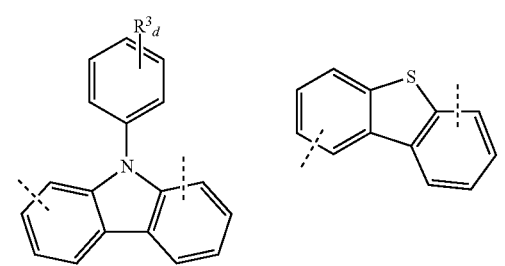
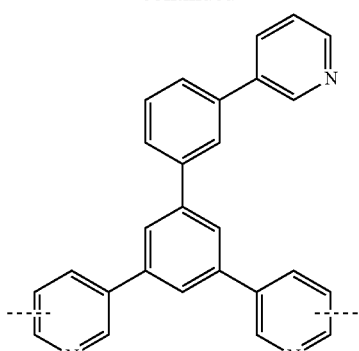
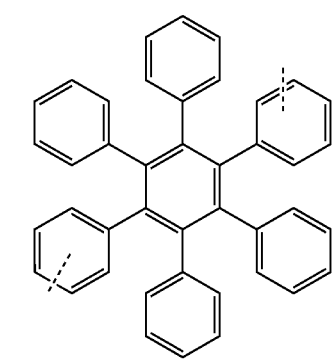
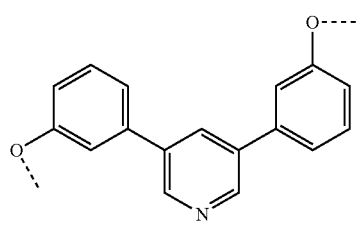
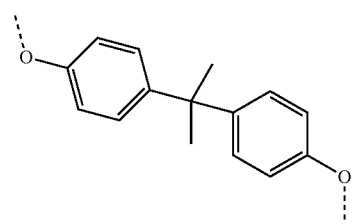
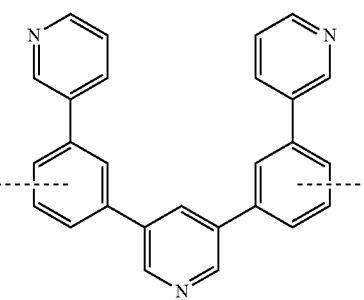

-continued

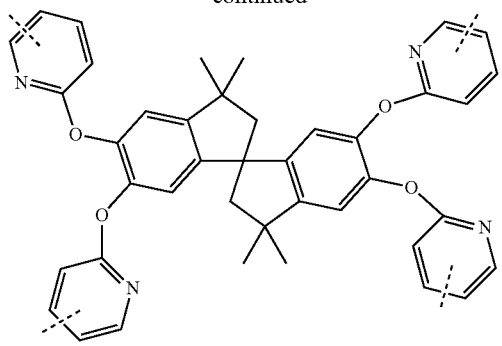

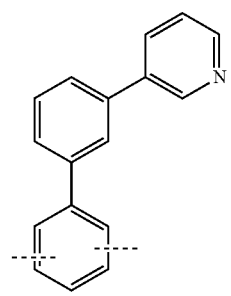

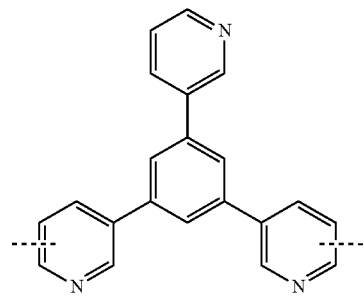

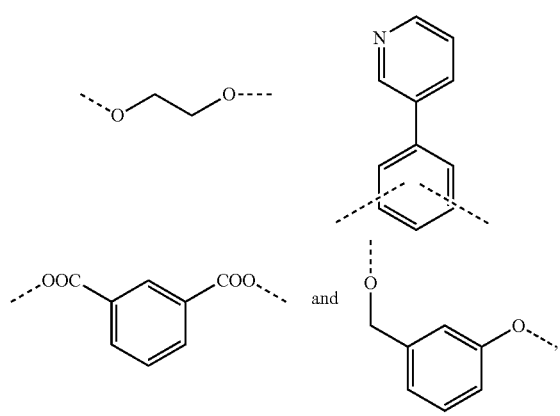

and

R² is, independently at each occurrence, a C₁-C₂₀ aliphatic radical, a C₃-C₂₀ aromatic radical, a C₃-C₂₀ cycloaliphatic radical, an aryl groups or a heteroaryl group, and R³ is, independently at each occurrence, a C₁-C₂₀ aliphatic radical, a C₃-C₂₀ aromatic radical, a C₃-C₂₀ cycloaliphatic radical, an aryl group or a heteroaryl group and d is an integer ranging from 0-5.

6. The compound according to claim 5, wherein Ar² is chosen from

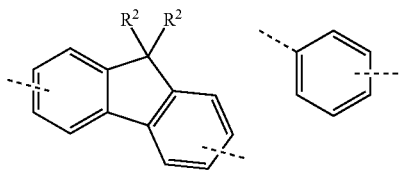

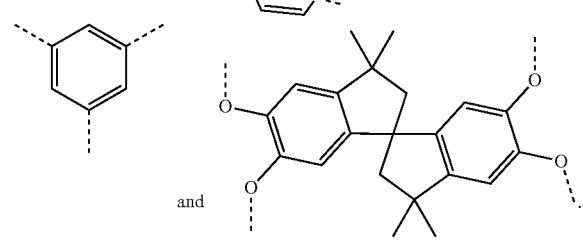

and

7. The compound according to claim 5, wherein Ar¹ and Ar² are independently chosen from

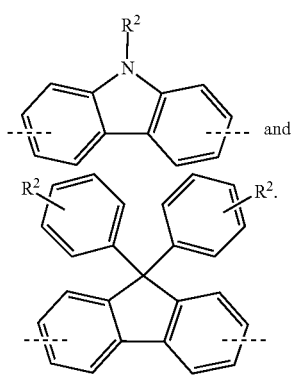

and

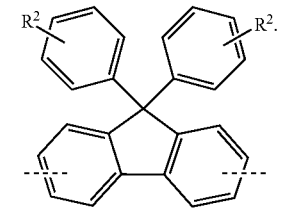

8. The compound according to claim 5, wherein Ar¹ and Ar² are independently chosen from

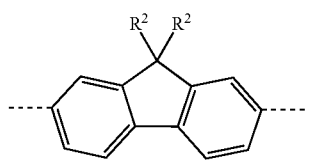

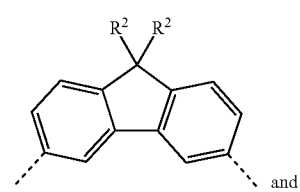

and

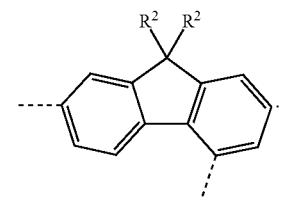

9. The compound according to claim 1, chosen from
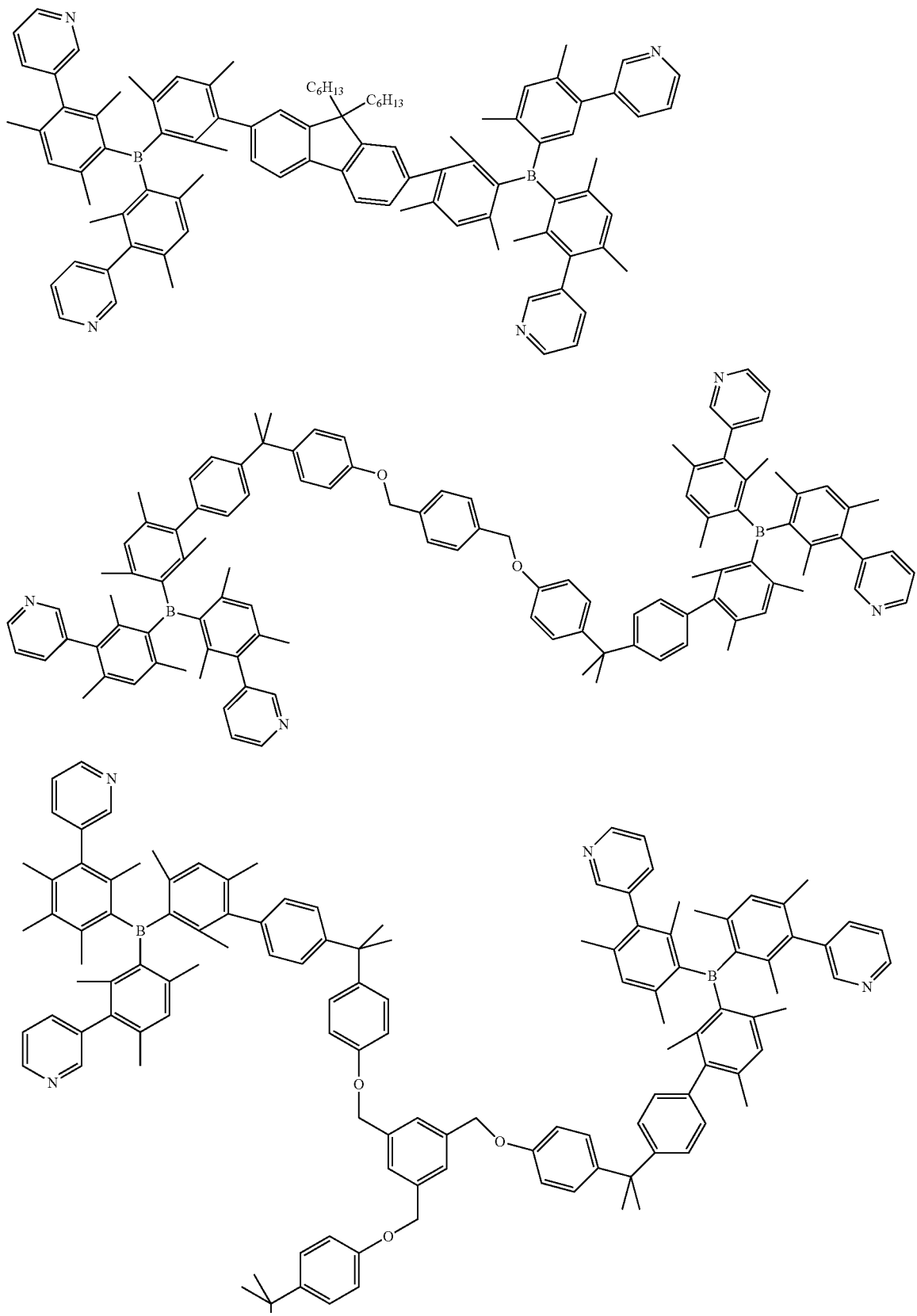

-continued
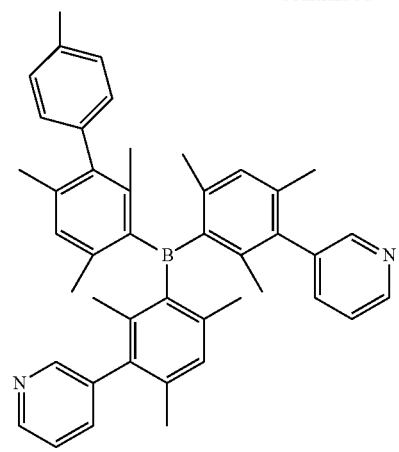
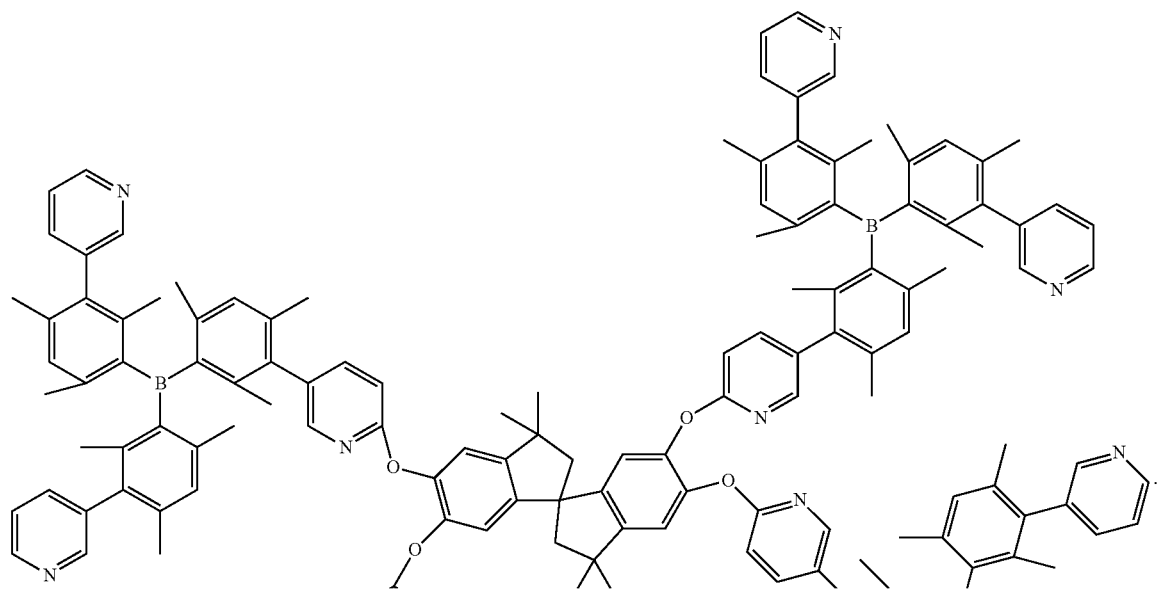
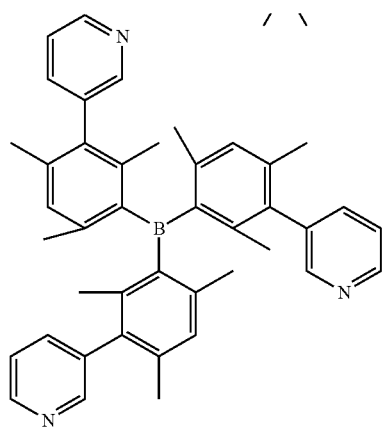
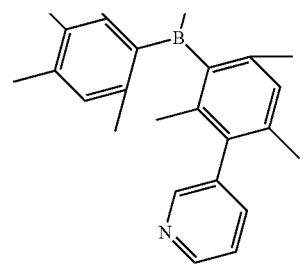

10. A compound of formula

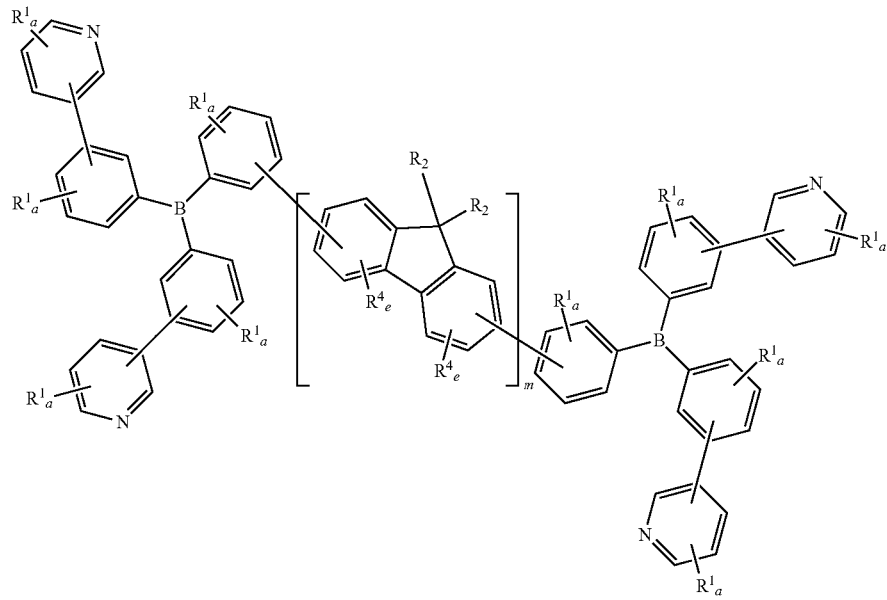

wherein

- $R^1$ is, independently at each occurrence, a $C_1$-$C_{20}$ aliphatic radical, a $C_3$-$C_{20}$ aromatic radical, or a $C_3$-$C_{20}$ cycloaliphatic radical;
- a is, independently at each occurrence, an integer ranging from 0-4;
- $R^2$ is, independently at each occurrence, a $C_1$-$C_{20}$ aliphatic radical, a $C_3$-$C_{20}$ aromatic radical, a $C_3$-$C_{20}$ cycloaliphatic radical, an alkyl, an aryl group or a heteroaryl group;
- $R^4$ is, independently at each occurrence, a $C_1$-$C_{20}$ aliphatic radical, a $C_3$-$C_{20}$ aromatic radical, a $C_3$-$C_{20}$ cycloaliphatic radical, an aryl group or a heteroaryl group;
- e is an integer ranging from 0-3; and
- m is an integer ranging from 1-7.

11. The compound according to claim 10, wherein $R^2$ is aryl or alkyl.

12. The compound according to claim 10, wherein $R^2$ is $C_6H_{13}$ or $C_8H_{17}$.

13. The compound according to claim 10, being of formula

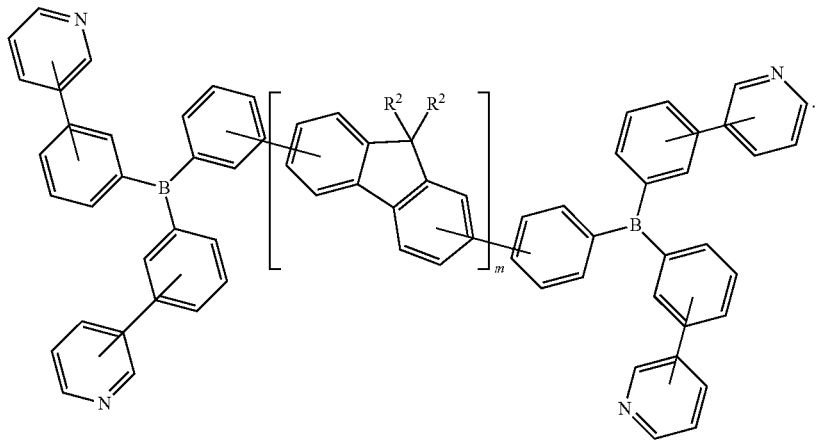

14. The compound according to claim 10, being of formula
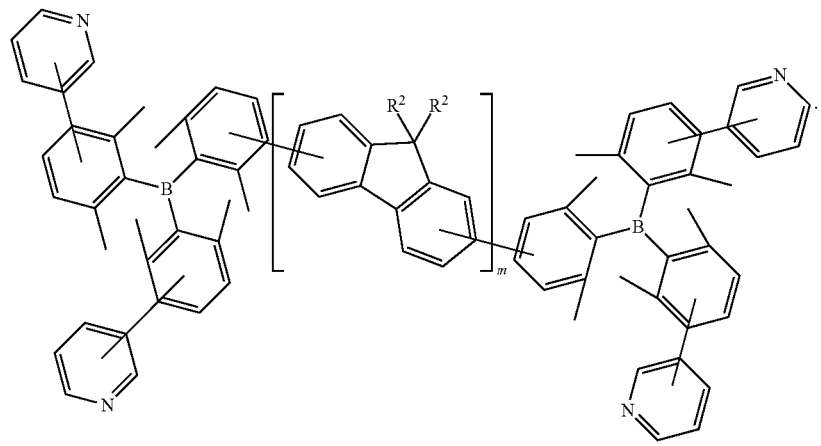
15. The compound according to claim 10, being of formula
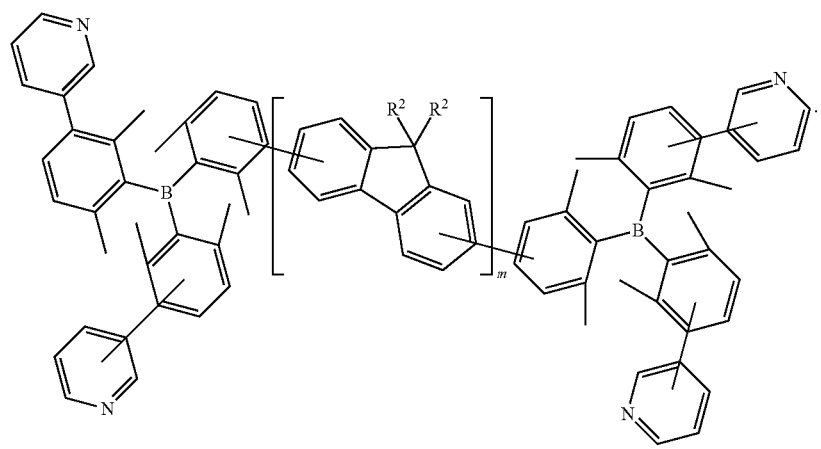
16. The compound according to claim 10, being of formula
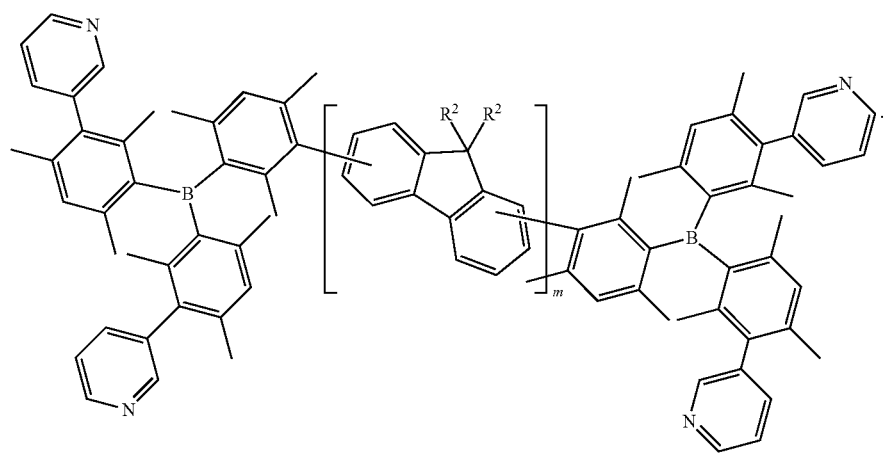

17. An optoelectronic device comprising at least one compound of formula I

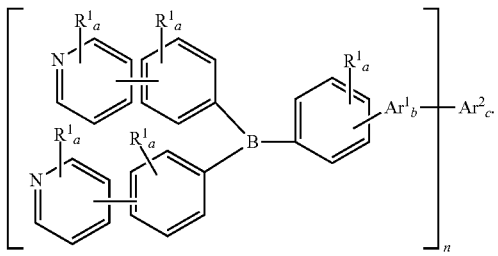

wherein
- $R^1$ is, independently at each occurrence, a $C_1$-$C_{20}$ aliphatic radical, a $C_3$-$C_{20}$ aromatic radical, or a $C_3$-$C_{20}$ cycloaliphatic radical;
- a is, independently at each occurrence, an integer ranging from 0-4;
- b is 0, 1 or 2;
- $Ar^1$ is a direct bond or heteroaryl, aryl, or alkyl or cycloalkyl;
- $Ar^2$ is heteroaryl, aryl, or alkyl or cycloalkyl;
- c is an integer ranging from 1-7; and
- n is an integer ranging from 2-4.

18. The optoelectronic device according to claim 17, wherein the at least one compound is of formula

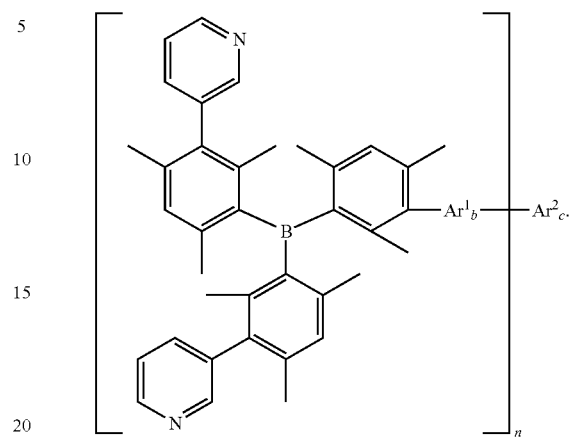

19. The optoelectronic device according to claim 17, being an organic light emitting device.

20. The optoelectronic device according to claim 19, having an electron transporting layer comprising the at least one compound of formula I.

21. The optoelectronic device according to claim 19, having a hole transporting layer comprising the at least one compound of formula I.

22. The optoelectronic device according to claim 19, having an emissive layer comprising the at least one compound of formula I.

23. The optoelectronic device according to claim 20, additionally comprising at least one of blue, yellow, orange, green and red phosphorescent dyes, or a combination thereof.

* * * * *